United States Patent
Umemoto et al.

(10) Patent No.: US 9,499,828 B2
(45) Date of Patent: Nov. 22, 2016

(54) PROTEIN HAVING GLYCOALKALOID BIOSYNTHETIC ENZYME ACTIVITY AND GENE ENCODING THE SAME

(75) Inventors: Naoyuki Umemoto, Sakura (JP); Katsunori Sasaki, Sakura (JP)

(73) Assignee: KIRIN HOLDINGS KABUSHIKI KAISHA, Tokyo (JP)

( * ) Notice: Subject to any disclaimer, the term of this patent is extended or adjusted under 35 U.S.C. 154(b) by 644 days.

(21) Appl. No.: 13/819,615

(22) PCT Filed: Aug. 30, 2011

(86) PCT No.: PCT/JP2011/069643
§ 371 (c)(1),
(2), (4) Date: Feb. 27, 2013

(87) PCT Pub. No.: WO2012/029804
PCT Pub. Date: Mar. 8, 2012

(65) Prior Publication Data
US 2013/0167271 A1  Jun. 27, 2013

(30) Foreign Application Priority Data
Aug. 31, 2010  (JP) .................. 2010-194590

(51) Int. Cl.
*A01H 1/04* (2006.01)
*C12N 15/82* (2006.01)
(Continued)

(52) U.S. Cl.
CPC ............. *C12N 15/8243* (2013.01); *A01H 1/04* (2013.01); *C12N 9/0004* (2013.01);
(Continued)

(58) Field of Classification Search
CPC .................. C12N 9/00; C12N 15/8243; C12N 15/8245; C12N 15/8218; C12N 15/8216; C12N 15/8241; A01H 15/8241; A01H 1/04; A01H 1/00; A01H 1/06
(Continued)

(56) References Cited

U.S. PATENT DOCUMENTS

| 5,959,180 A * | 9/1999 | Moehs ................. C12N 9/1051 435/320.1 |
| 2006/0168696 A1* | 7/2006 | Feldmann ............ C07K 14/415 800/287 |
| 2012/0159676 A1 | 6/2012 | Umemoto et al. |

FOREIGN PATENT DOCUMENTS

WO  2011/025011 A1  3/2011

OTHER PUBLICATIONS

Evertsz, E. M., et al. "Research Report Hybridization Cross-Reactivity within Homolo-gous Gene Families on Glass cDNA Microarrays." Biotechniques 31.5 (2001): 1182-1192.*
(Continued)

*Primary Examiner* — Russell Kallis
*Assistant Examiner* — Fan Weihua
(74) *Attorney, Agent, or Firm* — Sughrue Mion, PLLC

(57) ABSTRACT

Disclosed is the provision of a DNA for a glycoalkaloid biosynthetic enzyme in a plant belonging to the family Solanaceae such as potatoes. Also disclosed is a protein having the enzymatic activity of a glycoalkaloid biosynthetic enzyme of a plant belonging to the family Solanaceae such as potatoes and a method for producing and examining a novel organism using a gene encoding this protein.

7 Claims, 12 Drawing Sheets

(51) Int. Cl.
*C12N 9/02* (2006.01)
*C12Q 1/68* (2006.01)
*C12Q 1/527* (2006.01)

(52) U.S. Cl.
CPC .............. *C12N 9/0071* (2013.01); *C12Q 1/527* (2013.01); *C12Q 1/6895* (2013.01); *C12Q 2600/13* (2013.01); *C12Q 2600/156* (2013.01)

(58) Field of Classification Search
IPC ....................................................... C12N 9/00
See application file for complete search history.

(56) References Cited

OTHER PUBLICATIONS

Hijmans, Robert J., and David M. Spooner. "Geographic distribution of wild potato species." American Journal of Botany 88.11 (2001): 2101-2112.*
Ginzberg et al., 2009, "Potato steroidal glycoalkaloids: biosynthesis and genetic manipulation." Potato Research 52.1: 1-15.*
McCue, Kent F., et al. "The primary in vivo steroidal alkaloid glucosyltransferase from potato." Phytochemistry 67.15 (2006): 1590-1597.*
Li, X.Q., 2010, Detection of Nitrogen Sufficiency in Potato Plants Using Gene Expression Markers, Am. J. Potato Res. 87 (1):50-59.*
Anithakumari, A. M., et al. "A pipeline for high throughput detection and mapping of SNPs from EST databases." Molecular breeding 26.1 (2010): 65-75.*

Michael Campbell et al., "Dormancy in potato tuber meristems: chemically induced cessation in dormancy matches the natural process based on transcript profiles", Funct Integr Genomics, 2008, pp. 317-328, vol. 8, No. 4.
Database Sol Genomics Network [online], Unigene ID: SGN-U583521, Mar. 2009 <http://solgenomics.net/tools/sixframe_translate.pl?unigene_id=583521> Mar. 25, 2009 uploaded [retrieved on Oct. 13, 2011].
Mendel Friedman, "Potato Glycoalkaloids and Metabolites: Roles in the Plant and in the Diet", Journal of Agriculture and Food Chemistry, 2006, pp. 8655-8681, vol. 54.
Mendel Friedman, "Tomato Glycoalkaloids: Role in the Plant and in the Diet", Journal of Agriculture and Food Chemistry, 2002, pp. 5751-5780, vol. 50.
International Search Report for PCT/JP2011/069643 dated Oct. 25, 2011.
Communication for EP 11821819.7 dated Apr. 9, 2014, with Supplementary European Search Report dated Mar. 25, 2014.
Database Accession No. AK319823, entitled "Solanum Lycopersicum cDNA, clone: LEFL1002CA08, HTC in leaf", Abstract No. XP002722190, retrieved from EBI Accession No. EM_HTC:AK319823, http://;ibis.internal.epo.org/exam/dbfetch.jsp?id=EM_HTC:ak319823 dated Mar. 28, 2014.
Database Accession No. BERFK1, entitled "SubName: Full:Cytochrome P450 monooxygenase", Abstract No. XP002722189, retrieved from EBI Accession No. UNIPROT:B3RFK1, http://ibis.internal.epo.org/exam/dbfetch.jsp?id=UNIPROT:B3RFK1 dated Mar. 25, 2014.

* cited by examiner

Fig. 1-1

```
1st Nucleotide Sequence
  File Name        : potato E
  Sequence Size    : 1461
2nd Nucleotide Sequence
  File Name        : tomato E
  Sequence Size    : 1461
[94.589% / 1460 bp]    INT/OPT.Score : <  5366/  5366 >
     1' ATGGATTTCT ACAATTTAGC CTTATTCTTC ATAGCTTTAG TAATTGGGAT TTTCACATTT
        ********** ********** *** ****** ********** ** **** ** **********
     1" ATGGATTTCT ACAATTTAGC CTTGTTCTTC ATAGCTTTAA TACTTGGAAT TTTCACATTT 61' TATGCTATAT TAATGAGAAT TAATGGTTGG TATTATGCAA TCAAATTTTG TTCAAAGAAA
        ***  ****** ****** ****** ****** ** *
    61" TATGCCATAT TAATGAGAAT AAATGGTTGG TATTATGCAA TCAAATTTTG TTCAAACAAA 121' TATAACATCC CTCTAGGTTA TATGGGTTTG CCATATTTTG GCAACACACT TTCTTACTTC
        ********** *  *** ****** ******** * ****** ********
   121" TATAACATCC CAAATGGTTA TATGGGTTTG CCATATTTTG GTAACACACT TTCTTACTTC 181' AAATCTACCA TTTGTGGTGA TCCAAAATTCA TTCCTTGATT TCTTGCTAC TAGGTTTGGG
        *  * * * ******* ** * * ** ****** *******
   181" AAAGCTTCAA TGTGTGGTGA TCCAAAATCA TTCATTGATT TCTTGCTAC TAGGTTTGGA 241' ACAGGAGGAA TGTATAGGGC ATACATATTT GGGAAGCCAA CAATTATGGT GACAAAGCCA
        ***** ****** ****** ****** ****** ********
   241" GAAGGAGGAA TGTATAGGGC ATACATATTT GGGAAGCCAA CAATTATGGT GACAAAGCCA 301' GAAATAATTA GAAAAGTTTT GATGGATGAA GAATATCTTG AAAGAGGTTT GCCTAATTAT
        ******** ****** ******  **** ****** ********
   301" GAAATAATTA GAAAAGTTTT GATGGATGAA GAGTATCTTG AAAGAGGTTT GCCTAATTAT 361' ATGAAAAAAT TAATTGGATT AACAACTTCG ATTGAAGAAG ATAAATATTT TCGTCGATTA
        ******** ****** ******  ******* * ******  ***
   361" ATGAAAAAAT TAATTGGATT AACAACTTCG ATAGAAGAAG ACAAATATTT TCGTAGATTA 421' ACATCTCCAG TAAAAAGTCA TGGATTATTA TCCGATTATT TTGATTATAT CGATAAAACT
        *** * ** ****** ******  ******* * ****** ********
   421" ACAGCACCAG TAAAAAGTCA TGGATTATTA TCTGATTATT TCGATTATAT CGATAAAACT 481' GTGAGCACTA CATTAGAGAA ATACGCTACT ACGGAAGAAC CTATTGAGTT TCTCCATAAG
        *** * ******** ****** ******  **** * *****
   481" GTGAGTTCTA CATTAGAGAA ATACGCTACT ACGGAAGAAC CTGTTGAGTT TCTTCATAAA
```

Fig. 1-2

```
541'  ATGCACAGGC TTGCATTTGA GGTGTTTATG AGACTTCTTA TTGGTGATGA GGTTAATCAA
      ******* **  ** * ***** ********** ****** * * **********  *********
541"  ATGCACAAGC TTACGTTTGA GGTGTTTATG AGACTTTTAA TTGGTGATGA AGTTAATCAA

601'  GAATTTTTTG ATCAAATGTT TGTGGAGATT ACTGCTGTAA TTAGTGCTGT TCACAACTTG
      **** ****  ** ******* ** ****** ********** ****** *** ****** ***
601"  GAATTATTTG ATGAAATGTT TGAGGAGATT ACTGCTGTAA TTAGTGGTGT TCACAATTTG

661'  CCAATTAATC TCCCAGGATT TCCTTATCAT AAGGGACTCA AGGCTCGAAA AGTACTAGGA
      ********** ********** * ******** ********** ********** **********
661"  CCAATTAATC TCCCAGGATT TGCTTATCAT AAGGGACTCA AGGCTCGAAA AGTACTAGGA

721'  GGGATATTTC AAAAACTAAT AGATGAAAGA AGAGAAGCCA TGAAGGATGG AAAATCAATG
      * * *****  ***** **** ********** ********** ********** **********
721"  GAGGTATTTA AAAAATTAAT TGATGAAAGA AGAGAAGCCA TGAAGGATGG AAAATCAATG

781'  CCAAGGGCAA ACATAATTGA TATGTTGTTA TCAAACACTA ATCAAGATTA TGAAGACAAT
      **** ***** ********** ********** *******  * ********** *****  **
781"  CCAAAGGCAA ACATAATTGA TATGTTGTTA TCAAACAACA ATCAAGATTA TGAAGCAAAC

841'  ATATTGAGTG ACAAGAAGAT CGTTGAAATC CTAGTTTTGT TTTCATTTGC TGGTTTTGAA
      ** ******* ********** * ******** ********** ********** **********
841"  ATGTTGAGTG ACAAGAAGAT CATTGAAATC CTAGTTTTGT TTTCATTTGC TGGTTTTGAA

901'  CCTGTTGCTC TTATGTCTGT CAAGGCAATT TTTCACTTGC AAAAGCATCC CCATTTCTTG
      ********** ********** ********** ** ***** * **** *****  ********
901"  CCTGTTGCTC TTATGTCTGT CAAGGCAATT TTCCACTTAC AAAAACATCC ACATTTCTTG

961'  GAGAAAGCCA AAGAGGAACA AGAGGAAATA GTAAAGAGAA GAGCATCTTC AAATGCTGGA
      ** ******* ********** ********** ********** ********** **********
961"  GAAAAAGCCA AAGAGGAACA AGAGGAAATA GTAAAGAGAA GAGCATCTTC AAATGCTGGA

1021' CTTAGTTTTG ATGAGATTAG GCAAATGACG TTTGTTAGTA AGGTAATTAA TGAAACGTTA
      ********** **** *****  ********  ********** ** ******* **********
1021" CTTAGTTTTG ATGAAATTAG ACAAATGACA TTTGTTAGTA AGATAATTAA TGAAACGTTA

1081' CGTATTGCTA CTGATCAAAC GGTATTCCTT AGAGACACAA GTACTACTTT TAACATAAAT
      ***** **** *******  * ********** ********** ********** **********
1081" CGTATAGCTA CTGATCAGTC GGTATTCCTT AGAGACACAA GTACTACTTT TAACATAAAT

1141' GGGTACACCA TACCCAAAGG GTGGAAGTTT TTTGCAGTTA TATGGAATAT TCATATGAAT
      ********** ********** ********** ********** ********** **********
1141" GGGTACACCA TACCCAAAGG GTGGAAGTTT TTTGCAGTTG TATGGAATAT TCATATGAAT
```

Fig. 1-3

```
1201' CCTGATGTTT ATGTTCAGCC TAAGGAATTT AATCCTTCAA GATGGGATGA TATTGAAACT
      ********** ******* ** ********** ******** * ********** **********
1201" CCTGATGTTT ATGTTCAACC TAAGGAATTT AATCCTTCGA GATGGGATGA TATTGAAACT

1261' AAGCCAGGCA TTTTTCTTCC ATTTTCAATG GGCCCCAAAT CATGCCCAGG ATCCAATCTG
      ********** ******* **  ********** ********** ********** ******* **
1261" AAGCCAGGCA TTTTTCTACC TTTTTCAATG GGCCCCAAAT CATGCCCAGG ATCCAATTTG

1321' GCCAAGCTTC AAATTTCAGT AATTCTTCAT TATTATCTTC TTCACTACAG GGTTGAGCAA
      ********** ********** ********** ********** ********** **********
1321" GCCAAGCTTC AAATTTCAGT AATTCTTCAT TATTATCTTC TTCACTACAG GGTTGAGCAA

1381' ATTAATCCAG AGGCTAGATG TTATCCTCCT GAAAATTGTC TTGTGAAATT CAAGAAGCTC
      ********** ********** ********** ********** ********** *********
1381" ATTAATCCAG AGGCTAGATG TTATCCTCCT GAAAATTGTC TTGTGAAATT CAAGAAGCTA

1441' TCAATCTCTA GTGATGGTAA C
      ** ******* ** *******
1441" TCGATCTCTA GTAATGGTAA T
```

Fig. 3
A)
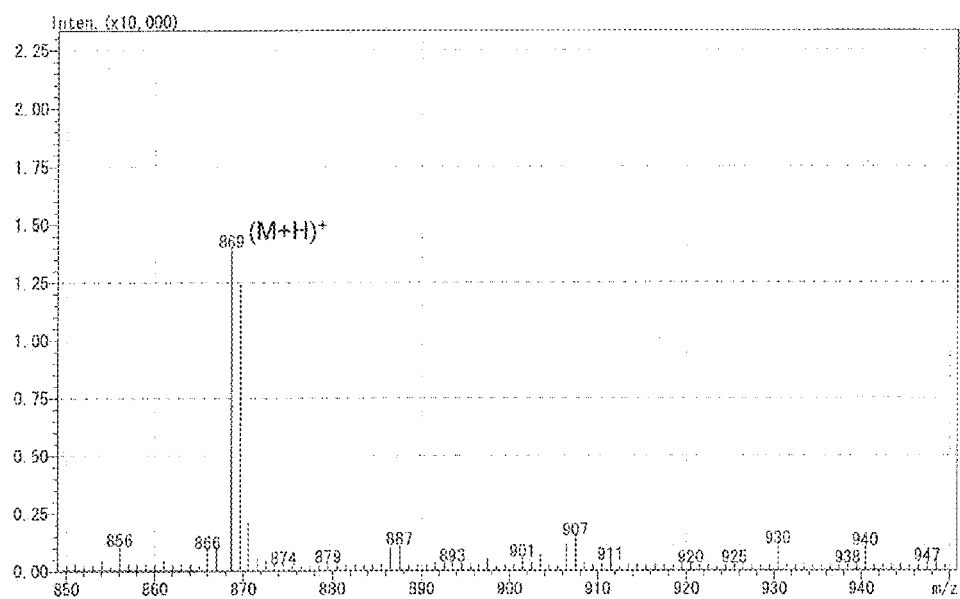
B)
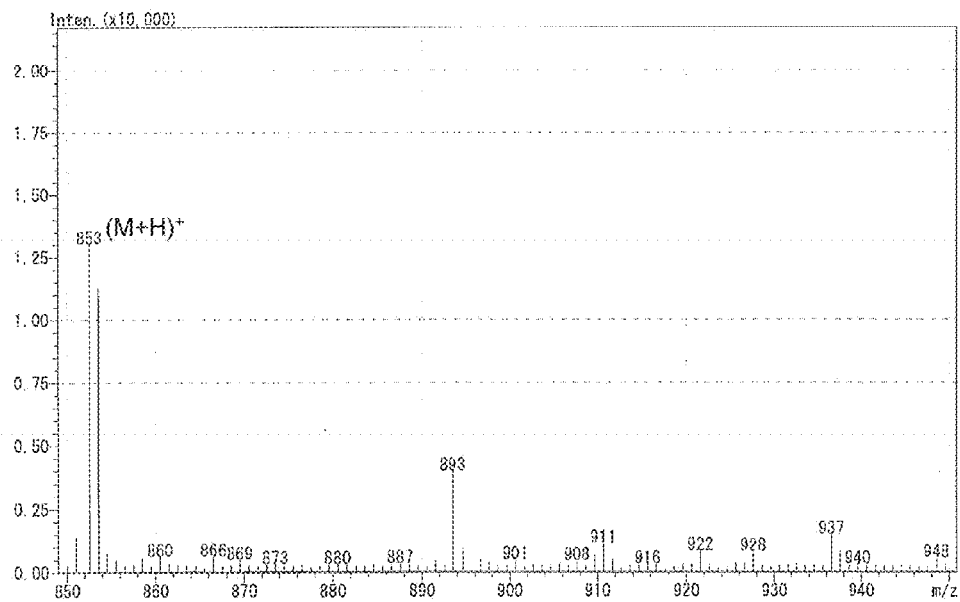

Fig. 4
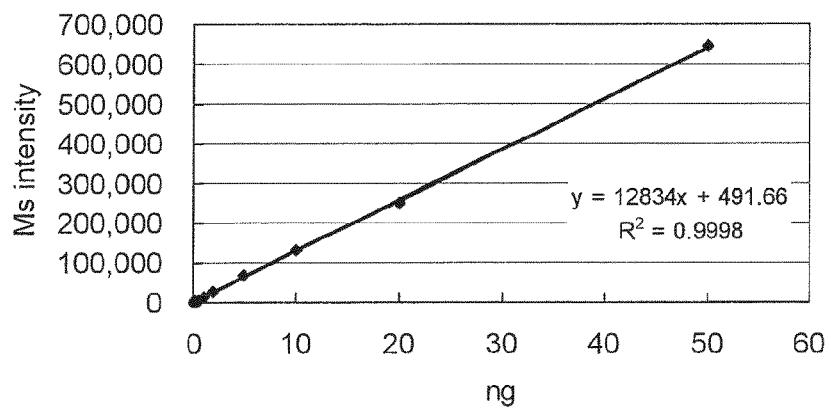
A)
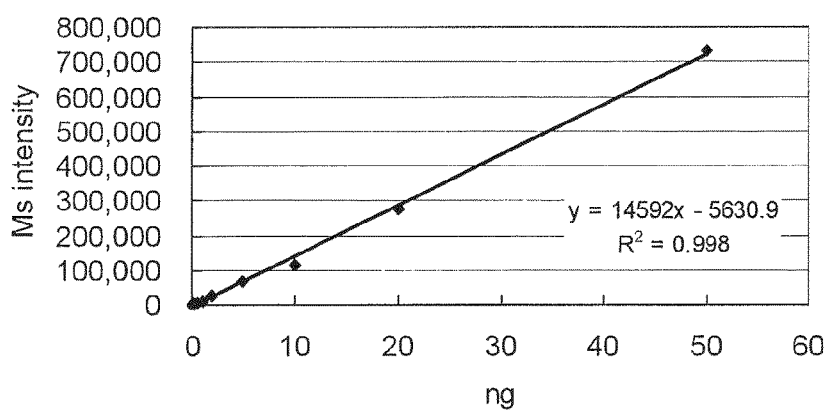
B)
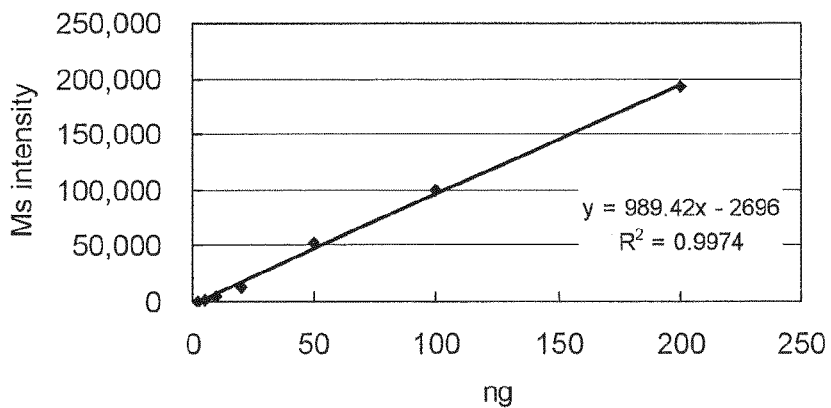
C)

1 2 3 4 5 6 7 8

1: Non-transformant
2: Non-transformant
3: pKT230 transformant #2
4: pKT230 transformant #8
5: pKT230 transformant #17
6: pKT230 transformant #22
7: pKT230 transformant #27
8: pKTt230 transformant #29

SEQUENCE LISTING

```
<160> NUMBER OF SEQ ID NOS: 19

<210> SEQ ID NO 1
<211> LENGTH: 487
<212> TYPE: PRT
<213> ORGANISM: Solanum tuberosum

<400> SEQUENCE: 1

Met Asp Phe Tyr Asn Leu Ala Leu Phe Phe Ile Ala Leu Val Ile Gly
1               5                   10                  15

Ile Phe Thr Phe Tyr Ala Ile Leu Met Arg Ile Asn Gly Trp Tyr Tyr
            20                  25                  30

Ala Ile Lys Phe Cys Ser Lys Lys Tyr Asn Ile Pro Leu Gly Tyr Met
        35                  40                  45

Gly Leu Pro Tyr Phe Gly Asn Thr Leu Ser Tyr Phe Lys Ser Thr Ile
    50                  55                  60

Cys Gly Asp Pro Asn Ser Phe Leu Asp Phe Phe Ala Thr Arg Phe Gly
65                  70                  75                  80

Thr Gly Gly Met Tyr Arg Ala Tyr Ile Phe Gly Lys Pro Thr Ile Met
                85                  90                  95

Val Thr Lys Pro Glu Ile Ile Arg Lys Val Leu Met Asp Glu Glu Tyr
            100                 105                 110

Leu Glu Arg Gly Leu Pro Asn Tyr Met Lys Lys Leu Ile Gly Leu Thr
        115                 120                 125

Thr Ser Ile Glu Glu Asp Lys Tyr Phe Arg Arg Leu Thr Ser Pro Val
    130                 135                 140

Lys Ser His Gly Leu Leu Ser Asp Tyr Phe Asp Tyr Ile Asp Lys Thr
145                 150                 155                 160

Val Ser Thr Thr Leu Glu Lys Tyr Ala Thr Thr Glu Glu Pro Ile Glu
                165                 170                 175

Phe Leu His Lys Met His Arg Leu Ala Phe Glu Val Phe Met Arg Leu
            180                 185                 190
```

```
Leu Ile Gly Asp Glu Val Asn Gln Glu Phe Asp Gln Met Phe Val
            195                 200                 205

Glu Ile Thr Ala Val Ile Ser Ala Val His Asn Leu Pro Ile Asn Leu
    210                 215                 220

Pro Gly Phe Pro Tyr His Lys Gly Leu Lys Ala Arg Lys Val Leu Gly
225                 230                 235                 240

Gly Ile Phe Gln Lys Leu Ile Asp Glu Arg Arg Glu Ala Met Lys Asp
                245                 250                 255

Gly Lys Ser Met Pro Arg Ala Asn Ile Ile Asp Met Leu Leu Ser Asn
                260                 265                 270

Thr Asn Gln Asp Tyr Glu Asp Asn Ile Leu Ser Asp Lys Lys Ile Val
            275                 280                 285

Glu Ile Leu Val Leu Phe Ser Phe Ala Gly Phe Glu Pro Val Ala Leu
    290                 295                 300

Met Ser Val Lys Ala Ile Phe His Leu Gln Lys His Pro His Phe Leu
305                 310                 315                 320

Glu Lys Ala Lys Glu Gln Glu Glu Ile Val Lys Arg Arg Ala Ser
                325                 330                 335

Ser Asn Ala Gly Leu Ser Phe Asp Glu Ile Arg Gln Met Thr Phe Val
                340                 345                 350

Ser Lys Val Ile Asn Glu Thr Leu Arg Ile Ala Thr Asp Gln Thr Val
            355                 360                 365

Phe Leu Arg Asp Thr Ser Thr Thr Phe Asn Ile Asn Gly Tyr Thr Ile
    370                 375                 380

Pro Lys Gly Trp Lys Phe Phe Ala Val Val Trp Asn Ile His Met Asn
385                 390                 395                 400

Pro Asp Val Tyr Val Gln Pro Lys Glu Phe Asn Pro Ser Arg Trp Asp
                405                 410                 415

Asp Ile Glu Thr Lys Pro Gly Ile Phe Leu Pro Phe Ser Met Gly Pro
                420                 425                 430

Lys Ser Cys Pro Gly Ser Asn Leu Ala Lys Leu Gln Ile Ser Val Ile
            435                 440                 445

Leu His Tyr Tyr Leu Leu His Tyr Arg Val Glu Gln Ile Asn Pro Glu
    450                 455                 460

Ala Arg Cys Tyr Pro Pro Glu Asn Cys Leu Val Lys Phe Lys Lys Leu
465                 470                 475                 480

Ser Ile Ser Ser Asp Gly Asn
                485

<210> SEQ ID NO 2
<211> LENGTH: 1461
<212> TYPE: DNA
<213> ORGANISM: Solanum tuberosum

<400> SEQUENCE: 2
atggatttct acaatttagc cttattcttc atagctttag taattgggat tttcacattt      60
tatgctatat taatgagaat taatggttgg tattatgcaa tcaaattttg ttcaaagaaa    120
tataacatcc ctctaggtta tatgggtttg ccatattttg caacacacact ttcttacttc   180 aaatctacca tttgtggtga tccaaattca ttccttgatt tctttgctac taggtttggg    240
acaggaggaa tgtataggc atacatattt gggaagccaa caattatggt gacaaagcca    300
gaaataatta gaaagttttt gatggatgaa gaatatcttg aaagaggttt gcctaattat    360
atgaaaaaat taattggatt aacaacttcg attgaagaag ataaatattt tcgtcgatta    420
```

```
acatctccag taaaaagtca tggattatta tccgattatt ttgattatat cgataaaact    480
gtgagcacta cattagagaa atacgctact acggaagaac ctattgagtt tctccataag    540
atgcacaggc ttgcatttga ggtgtttatg agacttctta ttggtgatga ggttaatcaa    600
gaattttttg atcaaatgtt tgtggagatt actgctgtaa ttagtgctgt tcacaacttg    660
ccaattaatc tcccaggatt tccttatcat aagggactca aggctcgaaa agtactagga    720
gggatatttc aaaaactaat agatgaaaga agagaagcca tgaaggatgg aaaatcaatg    780
ccaagggcaa acataattga tatgttgtta tcaaacacta atcaagatta tgaagacaat    840
atattgagtg acaagaagat cgttgaaatc ctagttttgt tttcatttgc tggttttgaa    900
cctgttgctc ttatgtctgt caaggcaatt tttcacttgc aaaagcatcc ccatttcttg    960
gagaaagcca agaggaaca agaggaaata gtaaagagaa gagcatcttc aaatgctgga   1020
cttagttttg atgagattag gcaaatgacg tttgttagta aggtaattaa tgaaacgtta   1080
cgtattgcta ctgatcaaac ggtattcctt agagacacaa gtactacttt taacataaat   1140
gggtacacca tacccaaagg gtggaagttt tttgcagttg tatggaatat tcatatgaat   1200
cctgatgttt atgttcagcc taaggaattt aatccttcaa gatgggatga tattgaaact   1260
aagccaggca ttttttcttcc attttcaatg ggccccaaat catgcccagg atccaatctg   1320
gccaagcttc aaatttcagt aattcttcat tattatcttc ttcactacag ggttgagcaa   1380
attaatccag aggctagatg ttatcctcct gaaaattgtc ttgtgaaatt caagaagctc   1440
tcaatctcta gtgatggtaa c                                             1461

<210> SEQ ID NO 3
<211> LENGTH: 487
<212> TYPE: PRT
<213> ORGANISM: Solanum lycopersicum

<400> SEQUENCE: 3

Met Asp Phe Tyr Asn Leu Ala Leu Phe Phe Ile Ala Leu Ile Leu Gly
1               5                   10                  15

Ile Phe Thr Phe Tyr Ala Ile Leu Met Arg Ile Asn Gly Trp Tyr Tyr
            20                  25                  30

Ala Ile Lys Phe Cys Ser Asn Lys Tyr Asn Ile Pro Asn Gly Tyr Met
        35                  40                  45

Gly Leu Pro Tyr Phe Gly Asn Thr Leu Ser Tyr Phe Lys Ala Ser Met
    50                  55                  60

Cys Gly Asp Pro Lys Ser Phe Ile Asp Phe Ala Thr Arg Phe Gly
65                  70                  75                  80

Glu Gly Gly Met Tyr Arg Ala Tyr Ile Phe Gly Lys Pro Thr Ile Met
                85                  90                  95

Val Thr Lys Pro Glu Ile Ile Arg Lys Val Leu Met Asp Glu Tyr
            100                 105                 110

Leu Glu Arg Gly Leu Pro Asn Tyr Met Lys Lys Leu Ile Gly Leu Thr
        115                 120                 125

Thr Ser Ile Glu Glu Asp Lys Tyr Phe Arg Arg Leu Thr Ala Pro Val
    130                 135                 140

Lys Ser His Gly Leu Leu Ser Asp Tyr Phe Asp Tyr Ile Asp Lys Thr
145                 150                 155                 160

Val Ser Ser Thr Leu Glu Lys Tyr Ala Thr Thr Glu Glu Pro Val Glu
                165                 170                 175

Phe Leu His Lys Met His Lys Leu Thr Phe Glu Val Phe Met Arg Leu
            180                 185                 190
```

```
Leu Ile Gly Asp Glu Val Asn Gln Glu Leu Phe Asp Glu Met Phe Glu
            195                 200                 205
Glu Ile Thr Ala Val Ile Ser Gly Val His Asn Leu Pro Ile Asn Leu
    210                 215                 220
Pro Gly Phe Ala Tyr His Lys Gly Leu Lys Ala Arg Lys Val Leu Gly
225                 230                 235                 240
Glu Val Phe Lys Lys Leu Ile Asp Glu Arg Arg Glu Ala Met Lys Asp
                245                 250                 255
Gly Lys Ser Met Pro Lys Ala Asn Ile Ile Asp Met Leu Leu Ser Asn
            260                 265                 270
Asn Asn Gln Asp Tyr Glu Ala Asn Met Leu Ser Asp Lys Lys Ile Ile
        275                 280                 285
Glu Ile Leu Val Leu Phe Ser Phe Ala Gly Phe Glu Pro Val Ala Leu
    290                 295                 300
Met Ser Val Lys Ala Ile Phe His Leu Gln Lys His Pro His Phe Leu
305                 310                 315                 320
Glu Lys Ala Lys Glu Glu Gln Glu Glu Ile Val Lys Arg Arg Ala Ser
                325                 330                 335
Ser Asn Ala Gly Leu Ser Phe Asp Glu Ile Arg Gln Met Thr Phe Val
            340                 345                 350
Ser Lys Ile Ile Asn Glu Thr Leu Arg Ile Ala Thr Asp Gln Ser Val
        355                 360                 365
Phe Leu Arg Asp Thr Ser Thr Thr Phe Asn Ile Asn Gly Tyr Thr Ile
    370                 375                 380
Pro Lys Gly Trp Lys Phe Ala Val Val Trp Asn Ile His Met Asn
385                 390                 395                 400
Pro Asp Val Tyr Val Gln Pro Lys Glu Phe Asn Pro Ser Arg Trp Asp
                405                 410                 415
Asp Ile Glu Thr Lys Pro Gly Ile Phe Leu Pro Phe Ser Met Gly Pro
            420                 425                 430
Lys Ser Cys Pro Gly Ser Asn Leu Ala Lys Leu Gln Ile Ser Val Ile
        435                 440                 445
Leu His Tyr Tyr Leu Leu His Tyr Arg Val Glu Gln Ile Asn Pro Glu
    450                 455                 460
Ala Arg Cys Tyr Pro Pro Glu Asn Cys Leu Val Lys Phe Lys Lys Leu
465                 470                 475                 480
Ser Ile Ser Ser Asn Gly Asn
                485

<210> SEQ ID NO 4
<211> LENGTH: 1461
<212> TYPE: DNA
<213> ORGANISM: Solanum lycopersicum

<400> SEQUENCE: 4
atggatttct acaatttagc cttgttcttc atagctttaa tacttggaat tttcacattt      60
tatgccatat taatgagaat aaatggttgg tattatgcaa tcaaattttg ttcaaacaaa     120
tataacatcc caaatggtta tatgggtttg ccatattttg gtaacacact ttcttacttc     180
aaagcttcaa tgtgtggtga tccaaaatca ttcattgatt tctttgctac taggtttgga     240
gaaggaggaa tgtataggc atacatattt gggaagccaa caattatggt gacaaagcca     300
gaaataatta gaaagttttt gatggatgaa gagtatcttg aaagaggttt gcctaattat     360
atgaaaaaat taattggatt aacaacttcg atagaagaag acaaatattt tcgtagatta     420
```

```
acagcaccag taaaaagtca tggattatta tctgattatt tcgattatat cgataaaact    480
gtgagttcta cattagagaa atacgctact acggaagaac ctgttgagtt tcttcataaa    540
atgcacaagc ttacgtttga ggtgtttatg agacttttaa ttggtgatga agttaatcaa    600
gaattatttg atgaaatgtt tgaggagatt actgctgtaa ttagtggtgt tcacaatttg    660
ccaattaatc tcccaggatt tgcttatcat aagggactca aggctcgaaa agtactagga    720
gaggtattta aaaaattaat tgatgaaaga agagaagcca tgaaggatgg aaaatcaatg    780
ccaaaggcaa acataattga tatgttgtta tcaaacaaca atcaagatta tgaagcaaac    840
atgttgagtg acaagaagat cattgaaatc ctagttttgt tttcatttgc tggttttgaa    900
cctgttgctc ttatgtctgt caaggcaatt ttccacttac aaaaacatcc acatttcttg    960
gaaaaagcca agaggaaca agaggaaata gtaaagagaa gagcatcttc aaatgctgga   1020
cttagttttg atgaaattag acaaatgaca tttgttagta agataattaa tgaaacgtta   1080
cgtatagcta ctgatcagtc ggtattcctt agagacacaa gtactacttt taacataaat   1140
gggtacacca tacccaaagg gtggaagttt tttgcagttg tatggaatat tcatatgaat   1200
cctgatgttt atgttcaacc taaggaattt aatccttcga gatgggatga tattgaaact   1260
aagccaggca ttttctacc ttttcaatg ggccccaaat catgcccagg atccaatttg   1320
gccaagcttc aaatttcagt aattcttcat tattatcttc ttcactacag ggttgagcaa   1380
attaatccag aggctagatg ttatcctcct gaaaattgtc ttgtgaaatt caagaagcta   1440
tcgatctcta gtaatggtaa t                                             1461

<210> SEQ ID NO 5
<211> LENGTH: 5439
<212> TYPE: DNA
<213> ORGANISM: Solanum tuberosum

<400> SEQUENCE: 5
gaggctaaga aaagagaga gagagaacat ggatttctac aatttagcct tattcttcat     60
agctttagta attgggattt tcacatttta tgctatatta atgagaatta atggttggta   120
ttatgcaatc aaattttgtt caagaaaata taacatccct ctaggttata tgggtttgcc   180
atattttggc aacacacttt cttacttcaa atctaccatt tgtggtgatc caaattcatt   240
ccttgatttc tttgctacta ggtaaattaa ctattttcat tatcgtactt atttgctatg   300
ttgtttgaat tcttgaaaaa tattaatatg tacttgtcaa atcttttaaa aatagtgcat   360
ttttgaagaa tctaacatga gtactgcaac tgttattaca attacatttt tgtagagtcc   420
aattgaacaa aatttttctt ttttttttt aaaggtttgg gacaggagga atgtataggg   480
catacatatt tgggaagcca acaattatgg tgacaaagcc agaaataatt agaaaagttt   540
tgatggatga agaatatctt gaaagaggtt tgcctaatta tatgaaaaaa ttaattggat   600
taacaacttc gattgaagaa gataaatatt ttcgtcgatt aacatctcca gtaaaaagtc   660
atggattatt atccgattat tttgattata tcgataaaac tgtgagcact acattagaga   720
aatacgctac tacggaagaa cctattgagt ttctccataa gatgcacagg cttgcatttg   780
aggtgtttat gagacttctt attggtgatg aggttaatca agaatttttt gatcaaatgt   840 tgtggagat tactgctgta attagtgctg ttcacaactt gccaattaat ctcccaggat   900
ttccttatca taagggactc aaggtaagat gtgttcaaac ttttaatatt atttttattt   960
cattttaaat tttaataat cataagatat aaatgtgttt tttaacttg ccatcagttt  1020
```

```
atatttgtgc ccttcaattt tgagtgtgta taaatttgaa ttagtagaca catgacataa      1080
tatatgtagg acatcatgta ggatgcaaac tgtcacgaag aacgtgtgtg tttacttgtt      1140
caactttata taagtttaag tgtctacttg tgtgtgtcca aaattgaagg gtacacatgt      1200
gagatgaggc caagttaaat ggcatattta tatattttag atagaataac atgttttttt      1260
ttatatacat aatatataaa tctgcccttc gatttggatt caactgacat ctatgccctc      1320
caactttagg tgtgcacaaa catatgctta aacatgtata aaaatgaaca aatagacaca      1380
tttgtcttaa ctggcacaca tgacaatttt gtgtcctacg tgatgcccta catgtattat      1440
gttacgcagg acatgtgtgt caacttgttt aatttatac aagtttaagt gtctatttgt       1500
acacacccaa aattagttga agccaagtta aatgacatat ttatgtatta tatattttct      1560
acatacataa ttacatgtgt gggagcccca accacctctt ttattttttt aataattggt      1620
gatggtggtg attagagaga ctagaattaa agatatttgt tctgttgtaa taccattatt      1680
gaattgtacg gctacttcat ttaaggaact attgatttaa tttaagtgca acactctttt      1740
cacaaatcaa gaactacgaa gggtgtgttt ggtatgaaag gaaaacattt tccagaaaat      1800
gcttttcaat tttctcatgt ttggttgggt aaaatgtttt ggaaatgttt tccaaatcaa      1860 cttatttttcc tcaaatttaa ggaaaatgac ttcccctcaa aaattaagaa aaacattttc      1920
caaaactctc ctacaacttt aaattacaat ttatatttttt tgaaaaaatc aatttttttt      1980
gttgaaaaaa aaattaaagc ttttttttaa aaaaaaaaa tcgacttcaa ttttttaattt      2040 tttttatccc accctcaccc cctactccct accccgccaa atcccctttcc accccacaaa      2100 aaaaattaag ttttttttta aaaatgtttt ccaatttaaa tttttatttt tcatcccacc      2160
ccctccctta ccctcgacct cctccccacc atccccccta cacccaaaaa attcaaaaaa      2220
taaagttggt tctaaaatat atttctaatt caaattctta tttttcatcc acccaccccc      2280
cggccagccc accccaccca aaaaaatta agtttgtttt taaaaaaata ttttttattt      2340 caaatttta ttttccacc ccaccccta cccgcgaccc ccatcagcc cccacccccc         2400 tccaaaaaa aatttaagtt tattttaaaa aaaatatttt caatttcatt ttttgttttt      2460
tcaccccacc ccctacccgc cagcctcacc ccccaaccc acctcccccc aaaaaaattt      2520 aagtttatttt taaaaaaaat attttcagtt tcaattcaaa aaattattct ctctagttag      2580
aataaaagat attttctcaa aaaaaaaaat cattcataaa tcaaacacat aaaaatcttt      2640
ttcgaaaaat attttatact caccaaccaa acatgagaaa ataagtccaa agtctactta      2700
ttttccagga aaacatttttc cttcataccg aacacacccg aaatcacccc tttcatcttt      2760
tatcgtgata tttgtggttg taataaacat aatatagagt gcaacatgca tgtcaaagac      2820
caaaaactat gagatcactc ttttcattta atatttatcg tgttgtatat gtttattatg      2880
atttcaggct cgaaaagtac taggagggat atttcaaaaa ctaatagatg aaagaagaga      2940
gaagcctgaa ggatggaaaa tcaatgccaa gggcaaacat aattgatgtg ttgttatcaa      3000
acactaatca agattatgaa gacaatatat tgagtgacaa gaagatcgtt gaaatcctag      3060
ttttgttttc atttgctggt tttgaacctg ttgctcttat gtctgtcaag gcaattttttc     3120 acttgcaaaa gcatcccat ttcttggaga aagccaaagt aagtactctt tattctgttt       3180
taggggtgtc atatgggtga gttaaactga atttggacag gtggactgag ttaattagtc      3240
caaaacttac ttggactaaa atggactaac aaacgagtca taaactcaac tcgtctaatt      3300
agacaggtta agttaaattt ggacgaatta aattgggcta agttaatatg tccaaaaatt      3360
tggggctaaa atgagataac aaaaggatca taactcaact cgtctaattg gtcgatccaa      3420
```

```
acctaagcgg gttgggtggg tagtgtattc acgagtggat ttgccacccc tagtttattt    3480
tattttatat gacgatattt gattaattat tttttttaaca ggaggaacaa gaggaaatag   3540
taaagagaag agcatcttca aatgctggac ttagttttga tgagattagg caaatgacgt    3600
ttgttagtaa ggtaagacaa tattatgatg ttatatactt tctataatag catttttata   3660
aataatacca ttatacaaaa agtcatcagt acaaataatt aaaaaaagaa gatgaagtga   3720
taatacaaaa attggactaa catgcattat tatttattaa tgttatctct tttaatattg   3780
acaggtaatt aatgaaacgt tacgtattgc tactgatcaa acggtattcc ttagagacac   3840
aagtactact tttaacataa atggttggta ctttgcctta ttcttttgta tttatattat   3900
tattttctat cgaaaaatca aaatacgaca aatattttga aacgacgaat aattcattca   3960
ttcatttatc tcttgtatgt gtagggtaca ccatacccaa agggtggaag ttttttgcag   4020
ttgtatggaa tattcatatg aatcctgatg tttatgttca gcctaaggaa tttaatcctt   4080
caagatggga tgtaagtgat atgcatctta attaattgtg tttaagaaaa aaattcactt   4140
tatttttttt ataatcaaga aatttttgag ggttaataat gtatgattca aaatatgtta   4200
cgtaataagt tgtgtttgcc ttttaccact ttgaatatta ggtattttat ttgcagtagg   4260
gtttaaactc atgacgagaa tttattta cataagaata ttagtaaaat tagctcataa    4320
aaatatgatt tgttcaatgt cttatttatt aattcaatta attttgactc atctaattta   4380
attcatctaa aaaatagtgc taggataata ataataataa taataaaatc ggaaatgtgc   4440
tctaaactag aaccacgccc tccactagga agaaaaaaaa ttgattaaca atctcttaac   4500
attcttcaaa cctaattttg aacctcggta tgttctccta ttttgagtta tagcctcgat   4560
gagttaaaga cgaatcatgt catatctagc taatcaattc ttttcaaatc ttcctcgatc   4620
tatctctacc tctccttaaa catcgttgtc aatcttttgt accttaggag taaaagatag   4680
gatattagtt gctttaccgt tctcaatggt acatagctaa aaagtgtatt atcatcagga   4740
caatgcatgt gttcctcctt ttgagatatc tgaactatct caatttaact ttttacgtta   4800
cgaaaatcat tcccacatta cttattactt aatgatcaag tgaaatttga caggatattg   4860
aaactaagcc aggcattttt cttccatttt caatgggccc caaatcatgc ccaggatcca   4920
atctggccaa gcttcaaatt tcagtaattc ttcattatta tcttcttcac tacaggtaat   4980
taaatagctt catacttata atatgaaaaa attaactaat tatattttga atattttatt   5040
ttattttctt accaaatatt ttcaagggga ctaaaatata tgaatttatt gtgaaattta   5100
taccaaaaaa taagtatttt gacccttata ctcgtgattt tatcgtatga attgagatgg   5160
atggaatatt taaataaaa aaggaaatat aaattattga ttaaatcata ttttaattta   5220
attaaacgat atatttaata ttcatgcagg gttgagcaaa ttaatccaga ggctagatgt   5280
tatcctcctg aaaattgtct tgtgaaattc aagaagctct caatctctag tgatggtaac   5340 taatttttaat cattgtgcta caaataaata attcatgttg taatcttgaa aacaataagt   5400
gtattgaata attattaaat tggatgtttt tgtagaacg                          5439
```

<210> SEQ ID NO 6
<211> LENGTH: 24
<212> TYPE: DNA
<213> ORGANISM: Artificial
<220> FEATURE:
<223> OTHER INFORMATION: primer

<400> SEQUENCE: 6
gaggctaaga aaaagagaga gaga                                           24

<210> SEQ ID NO 7
<211> LENGTH: 23
<212> TYPE: DNA
<213> ORGANISM: Artificial
<220> FEATURE:
<223> OTHER INFORMATION: primer

<400> SEQUENCE: 7
cgttctacaa aaacatccaa ttt                                            23

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
tgataaggaa atcctgggag a                                              21

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
agagaagcca tgaaggatgg                                                20

<210> SEQ ID NO 10
<211> LENGTH: 24
<212> TYPE: DNA
<213> ORGANISM: Artificial
<220> FEATURE:
<223> OTHER INFORMATION: primer

<400> SEQUENCE: 10
gaaatacgct actacggaag aacc                                           24

<210> SEQ ID NO 11
<211> LENGTH: 21
<212> TYPE: DNA
<213> ORGANISM: Artificial
<220> FEATURE:
<223> OTHER INFORMATION: primer

<400> SEQUENCE: 11
cgtcatttgc ctaatctcat c                                              21

<210> SEQ ID NO 12
<211> LENGTH: 29
<212> TYPE: DNA
<213> ORGANISM: Artificial
<220> FEATURE:
<223> OTHER INFORMATION: primer

<400> SEQUENCE: 12
gagctctaga ggtttgggac aggaggaat                                      29

<210> SEQ ID NO 13
<211> LENGTH: 29
<212> TYPE: DNA
<213> ORGANISM: Artificial

-continued

```
<220> FEATURE:
<223> OTHER INFORMATION: primer

<400> SEQUENCE: 13
ggatccatat gcaagcctgt gcatcttat                                29

<210> SEQ ID NO 14
<211> LENGTH: 19
<212> TYPE: DNA
<213> ORGANISM: Artificial
<220> FEATURE:
<223> OTHER INFORMATION: primer

<400> SEQUENCE: 14
taaagcacga ggaagcggt                                           19

<210> SEQ ID NO 15
<211> LENGTH: 19
<212> TYPE: DNA
<213> ORGANISM: Artificial
<220> FEATURE:
<223> OTHER INFORMATION: primer

<400> SEQUENCE: 15
gcacaacaga caatcggct                                           19

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
taagggactc aaggctcgaa                                          20

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
ttcctctttg gctttctcca                                          20

<210> SEQ ID NO 18
<211> LENGTH: 19
<212> TYPE: DNA
<213> ORGANISM: Artificial
<220> FEATURE:
<223> OTHER INFORMATION: primer

<400> SEQUENCE: 18
taaagcacga ggaagcggt                                           19

<210> SEQ ID NO 19
<211> LENGTH: 19
<212> TYPE: DNA
<213> ORGANISM: Artificial
<220> FEATURE:
<223> OTHER INFORMATION: primer

<400> SEQUENCE: 19
gcacaacaga caatcggct                                           19
```

PROTEIN HAVING GLYCOALKALOID BIOSYNTHETIC ENZYME ACTIVITY AND GENE ENCODING THE SAME

CROSS REFERENCE TO RELATED APPLICATIONS

This application is a National Stage of International Application No. PCT/JP2011/069643 filed Aug. 30, 2011, claiming priority based on Japanese Patent Application No. 2010-194590 filed Aug. 31, 2010, the contents of all of which are incorporated herein by reference in their entirety.

TECHNICAL FIELD

The present invention relates to a production method for producing a glycoalkaloid compound characteristic of a plant belonging to the family Solanaceae such as potatoes, a glycoalkaloid biosynthetic enzyme, a DNA encoding the glycoalkaloid biosynthetic enzyme, a method for breeding and selecting a novel plant belonging to the family Solanaceae such as potatoes using the DNA, and a plant belonging to the family Solanaceae such as potatoes that does not produce a glycoalkaloid.

BACKGROUND ART

Glycoalkaloids refer to a group of plant-derived compounds, which are also called steroidal alkaloids. The glycoalkaloid structure is composed of $C_{27}$ isoprenoids containing a nitrogen atom, and it has been reported that there are 422 compounds of glycoalkaloids from plants belonging to the genus Solanum (Non Patent Literature 1, chapter 7.8). As to a plant belonging to the family Solanaceae other than those belonging to the genus Solanum, some plants belonging to the family Liliaceae are also known to contain glycoalkaloids. Among glycoalkaloids, important ones are chaconine and solanine from potatoes (Solanum tuberosum), and tomatine from tomatoes (Solanum lycopersicum), which belong to the genus Solanum of the family Solanaceae.

The potato is the world's forth largest crop produced, following maize, rice, and wheat. However, it is a well-known fact that buds sprouting from the tubers and the aerial parts of the plant contain chaconine and solanine, which are toxic substances. Chaconine and solanine cause poisoning symptoms such as abdominal pain, vertigo, and mild disturbance of consciousness. Also, chaconine and solanine easily accumulate in the tubers as a result of damage or exposure to sunlight; therefore, there is a risk that faulty handling of tubers may lead to an episode of accidental poisoning.

Accidental poisoning is occasionally observed, and in a recent case, there was an episode of accidental glycoalkaloid poisoning in an elementary school in Nara-city, Japan, on Jul. 16, 2009 (reported by Asahi.com). Potatoes are normally safe foodstuffs as the tubers are handled so that the glycoalkaloid levels are kept at 20 mg/100 g or less by, for example, dark storage of the tubers. However, in consideration of the risk of accidental poisoning such as the aforementioned event, reduction of glycoalkaloids in potatoes is a matter of concern to anybody involved in the handling of potatoes such as breeding, production, storage, transportation, sales, and purchasing of potatoes. Nevertheless, reduction of glycoalkaloids in potatoes has not been successful up to now. The reasons for this are that there is no wild potato species free from glycoalkaloid, and also, because the biosynthetic pathway of glycoalkaloids remains uncertain (Non Patent Literature 1, Figure 7.24 A and B, and Non Patent Literature 2), little progress has been made in the identification of genes involved in the biosynthetic pathway.

While glycoalkaloids have toxicity such as a cholinesterase inhibitory activity and a membrane disrupting effect, they are also known to have medical actions such as an anti-cancer activity, a liver-protection effect, an antispasmodic effect, an immune system-promoting effect, an antifungal effect, an antiprotozoal effect, and a molluscicidal activity (Non Patent Literature 1). It is also reported that esculeoside A, which is a metabolic product of glycoalkaloid in tomatoes, exhibits an anti-arteriosclerotic action (Non Patent Literature 3). However, since the biosynthetic pathway remains unknown, little progress has been made in research and development of inhibition or efficient production of metabolic products.

Recently, there are some reports on genes involved in the transglycosylation process after the production of aglycone (Non Patent Literatures 4 to 6). However, although Non Patent Literature 4 reports the gene of UDP-galactosyltransferase, which mediates the conversion of solanidine, which is an aglycone, to γ-solanine, and reports a strain in which the gene is suppressed, chaconine is not suppressed at all (Non Patent Literature 4, Figure 2). Non Patent Literature 4 reports the gene of UDP-glucosyltransferase, which mediates the conversion of solanidine to γ-chaconine, and reports a strain in which the gene is suppressed, either of chaconine or solanine is hardly suppressed (Non Patent Literature 5, Figure 5). Non Patent Literature 6 reports the gene of rhamnosyltransferase, which mediates the conversion of β-chaconine to α-chaconine, and β-solanine to α-solanine, showing that although the α form is decreased, the β and γ forms are increased. As shown above, it is understood that although the molecular species of glycoalkaloids can be changed also by inhibition of the transglycosylation process, control of the total amount of glycoalkaloids is extremely difficult.

There is a report of an attempt to reduce glycoalkaloids through overexpression of genes involved in the biosynthesis of plant sterols and plant hormones (Non Patent Literature 7). However, the amount of glycoalkaloids has only been reduced by about half at most (Non Patent Literature 7, Figure 5).

CITATION LIST

Non Patent Literature

Non Patent Literature 1: Eich, Solanaceae and Convolvulaceae: Secondary Metabolite (2008), Springer
Non Patent Literature 2: Ginzberg et al., Potato Research (2009) 52: 1-15
Non Patent Literature 3: Fujiwara et al., Annual Meeting of Japan Society for Bioscience, Biotechnology, and Agrochemistry, 2008, Abstract 2B07, p 22
Non Patent Literature 4: McCue et al., Plant Sci. (2005) 168: 267-273
Non Patent Literature 5: McCue et al., Phytochemistry (2006) 67: 1590-1597
Non Patent Literature 6: McCue et al., Phytochemistry (1998) 68: 327-334
Non Patent Literature 7: Amqvist et al., Plant Physiol. (2003) 131: 1792-1799

SUMMARY OF INVENTION

Technical Problem

The present invention aims to provide a production method for producing a glycoalkaloid compound characteristic of a plant belonging to the family Solanaceae such as potatoes, a glycoalkaloid biosynthetic enzyme, a DNA encoding the glycoalkaloid biosynthetic enzyme, a method for breeding and selecting a novel plant belonging to the family Solanaceae such as potatoes using the DNA, and a plant belonging to the family Solanaceae such as potatoes that does not produce a glycoalkaloid.

Solution to Problem

The present inventors conducted intensive studies to achieve the aforementioned aims. First of all, the present inventors took a close look at the stage prior to aglycone formation. They discovered a candidate gene involved in the above biosynthetic pathway in silico, and suppressed the expression of the endogenous candidate gene by causing expression of parts of the candidate genes to induce RNAi. As a result, they successfully obtained a potato transformant having a greatly reduced glycoalkaloid content, and at the same time identified the glycoalkaloid biosynthetic enzyme gene. Also, they demonstrated acquisition of a glycoalkaloid-free plant belonging to the family Solanaceae such as potatoes by selecting a plant in which the expression of the above gene is suppressed. They also demonstrated that production of a novel glycoalkaloid compound was possible by expressing the above gene, and further demonstrated that analysis of the polymorphism was made possible by comparing the genomic sequence of the above gene among a variety of plants belonging to the family Solanaceae such as potatoes, whereby a newly bred plant belonging to the family Solanaceae such as potatoes can be established as a variety. The present invention was completed based on the foregoing findings. In a similar manner, they also successfully created tomatoes having a reduced glycoalkaloid content by suppressing the endogenous gene.

That is, the present invention encompasses the following inventions.

[1] A protein of the following (a) or (b):
(a) a protein consisting of the amino acid sequence shown in SEQ ID NO: 1; and
(b) a protein consisting of the amino acid sequence shown in SEQ ID NO: 1 with deletion, substitution, insertion, or addition of one or several amino acids, and having a glycoalkaloid biosynthetic enzyme activity.

[2] A gene consisting of a DNA of any one of the following (c) to (f):
(c) a DNA consisting of the nucleotide sequence shown in SEQ ID NO: 2;
(d) a DNA hybridizing to a DNA consisting of a nucleotide sequence complimentary to the DNA consisting of the nucleotide sequence shown in SEQ ID NO: 2 under a stringent condition and encoding a protein having a glycoalkaloid biosynthetic enzyme activity;
(e) a DNA consisting of a nucleotide sequence having 80% or more sequence identity with the nucleotide sequence shown in SEQ ID NO: 2 and encoding a protein having a glycoalkaloid biosynthetic enzyme activity; and
(f) a DNA consisting of a degenerate isomer of the nucleotide sequence shown in SEQ ID NO: 2.

[3] A protein of the following (g) or (h):
(g) a protein consisting of the amino acid sequence shown in SEQ ID NO: 3; and
(h) a protein consisting of the amino acid sequence shown in SEQ ID NO: 3 with deletion, substitution, insertion, or addition of one or several amino acids, and having a glycoalkaloid biosynthetic enzyme activity.

[4] A gene consisting of a DNA of any one of the following (i) to (l);
(i) a DNA consisting of the nucleotide sequence shown in SEQ ID NO: 4;
(j) a DNA hybridizing to a DNA consisting of a nucleotide sequence complimentary to the DNA consisting of the nucleotide sequence shown in SEQ ID NO: 4 under a stringent condition and encoding a protein having a glycoalkaloid biosynthetic enzyme activity;
(k) a DNA consisting of a nucleotide sequence having 80% or more sequence homology with the nucleotide sequence shown in SEQ ID NO: 4 and encoding a protein having a glycoalkaloid biosynthetic enzyme activity; and
(l) a DNA consisting of a degenerate isomer of the nucleotide sequence shown in SEQ ID NO: 4.

[5] A recombinant vector comprising the gene according to [2] or [4].

[6] A transformant into which the recombinant vector according to [5] is introduced.

[7] The transformant according to [6], which is a plant.

[8] A method for detecting a presence of a mutation and/or polymorphism in a gene encoding a glycoalkaloid biosynthetic enzyme in a plant, comprising the steps of:
(i) isolating a nucleic acid from a plant, the nucleic acid being a genomic DNA or an RNA;
(ii) when the nucleic acid in (i) is the RNA, synthesizing a cDNA by reverse transcription;
(iii) amplifying a gene fragment comprising a nucleotide sequence shown in SEQ ID NO: 2, 4, or 5 from the DNA obtained by the step (i) or (ii); and
(iv) determining a presence of a mutation and/or polymorphism in the DNA.

[9] The method according to [8], wherein the plant is a plant belonging to the family Solanaceae such as potatoes.

[10] A method for selecting a plant comprising a mutation and/or polymorphism, comprising detecting a mutation and/or polymorphism in a gene encoding a glycoalkaloid biosynthetic enzyme by the method according to [8] or [9].

[11] A plant comprising a mutation and/or polymorphism in a gene encoding a glycoalkaloid biosynthetic enzyme, wherein the plant is selected by the method according to [10].

[12] The plant according to [11], which is a plant belonging to the family Solanaceae such as potatoes.

[13] A method for selecting a plant according to [8] or [9], comprising selecting a plant in which an ability to express a gene encoding a glycoalkaloid biosynthetic enzyme or an activity of a glycoalkaloid biosynthetic enzyme encoded by the gene is altered from that in an existing variety.

[14] A plant in which an ability to express a gene encoding a glycoalkaloid biosynthetic enzyme or an activity of a glycoalkaloid biosynthetic enzyme encoded by the gene is altered from that in an existing variety, wherein the plant is selected by the method according to [13].

[15] The plant according to [14], which is a plant belonging to the family Solanaceae such as potatoes.

The present specification encompasses the contents of the description of the specification and/or drawings of JP patent Application No. 2010-194590, based on which the present application claims priority.

Advantageous Effects of Invention

According to the present invention, the expression of the activity of a protein acting to biosynthesize a glycoalkaloid compound characteristic of a plant belonging to the family Solanaceae such as potatoes and the expression of the activity of the gene encoding this protein can be regulated. That is, a method for producing a plant in which the activity of the above gene is regulated and a plant belonging to the family Solanaceae such as potatoes that does not produce a glycoalkaloid are provided. The present invention enables breeding of a plant belonging to the family Solanaceae such as potatoes characterized by containing a glycoalkaloid compound. The enzyme of the present invention enables mass-production of glycoalkaloid compounds exhibiting various beneficial physiological activities at low cost.

BRIEF DESCRIPTION OF DRAWINGS

FIG. 1-1 shows the results of the analysis of the homology of the biosynthetic gene E between potatoes (SEQ ID NO: 2) and tomatoes (SEQ ID NO: 4) by the DNA analysis software GENETYX (GENETYX CORPORATION). The overall results indicate very high homology.

FIG. 1-2 shows the results of the analysis of the homology of the biosynthetic gene E between potatoes (SEQ ID NO: 2) and tomatoes (SEQ ID NO: 4) by the DNA analysis software GENETYX (GENETYX CORPORATION) (Continued from FIG. 1-1).

FIG. 1-3 shows the results of the analysis of the homology of the biosynthetic gene E between potatoes (SEQ ID NO: 2) and tomatoes (SEQ ID NO: 4) by the DNA analysis software GENETYX (GENETYX CORPORATION) (Continued from FIG. 1-2).

FIG. 2 shows the construction of a vector for suppression of the candidate E gene, showing the construction of the region between the right border (RB) and left border (LB) and the restriction enzyme sites of T-DNA, which is the gene segment to be introduced.

FIG. 3 shows A) an MS spectrum indicating the protonated parent ion peak $(M+H)^+$ for α-solanine and B) an MS spectrum for the protonated parent ion peak $(M+H)^+$ for α-chaconine.

FIG. 4 shows A) a calibration curve (LC-MS quantitative analysis system) for α-solanine, B) a calibration curve (LC-MS quantitative analysis system) for α-chaconine, and C) a calibration curve (LC-MS quantitative analysis system) for brassinolide.

DESCRIPTION OF EMBODIMENTS

Figure 2:
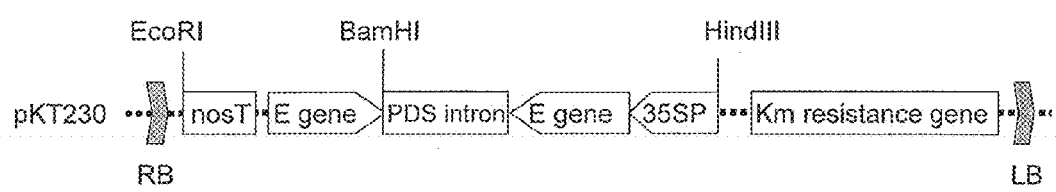

Hereinbelow, the present invention will be described in detail.
1. Novel Glycoalkaloid Biosynthetic Enzyme The protein and enzyme of the present invention refer to a glycoalkaloid biosynthetic enzyme contained in a plant belonging to the family Solanaceae such as potatoes. The family Solanaceae such as potatoes includes potatoes (*Solanum tuberosum*), tomatoes (*Solanum lycopersicum*), eggplants (*Solanum melongena*), chili peppers (*Capsicum annuum*), and the like. Also, the enzyme of the present invention refers to a membrane-bound cytochrome P450 monooxidase. The glycoalkaloid obtained using the enzyme of the present invention includes a glycoalkaloid synthesized in a plant belonging to the family Solanaceae such as potatoes, and examples thereof include a glycoalkaloid in potatoes such as chaconine and solanine and a glycoalkaloid in tomatoes such as tomatine.

Examples of a preferable steroid compound serving as a substrate for the glycoalkaloid biosynthetic enzyme of the present invention include cholesterols. Examples of the cholesterols include cholesterol, sitosterol, campesterol, stigmasterol, and brassicasterol. The glycoalkaloid biosynthetic enzyme of the present invention is a hydroxylase that transfers a hydroxyl group to the above cholesterols.

The full-length amino acid sequence of the enzyme of the present invention is shown in SEQ ID NO: 1 or 3. Further, the protein of the present invention encompasses a protein having a substantially identical amino acid sequence to the amino acid sequence shown in SEQ ID NO: 1 or 3 and having a glycoalkaloid biosynthetic enzyme activity. Here, examples of the substantially identical amino acid sequence include the amino acid sequence shown in SEQ ID NO: 1 or 3 with deletion, substitution, insertion, and/or addition of one or several amino acids (1 to 10 amino acids, preferably 1 to 7 amino acids, more preferably 1 to 5 amino acids, even more preferably 1 to 3 amino acids, and still more preferably 1 or 2 amino acids) or an amino acid sequence having at least 85% or more, preferably 90% or more, more preferably 95% or more, and particularly preferably 97% or more sequence identity with the above amino acid sequence by calculation using, for example, Basic Local Alignment Search Tool at the National Center for Biological Information (BLAST) based on, for example, default, namely initially set parameters.

The glycoalkaloid biosynthetic enzyme of the present invention encompasses a naturally occurring glycoalkaloid biosynthetic enzyme isolated from a plant and a recombinant glycoalkaloid biosynthetic enzyme produced by the genetic engineering technique.
2. Gene Encoding the Glycoalkaloid Biosynthetic Enzyme The gene of the present invention refers to a gene encoding a glycoalkaloid biosynthetic enzyme acting to connect a hydroxyl group to a steroid compound, and a gene encoding a protein having the aforementioned glycoalkaloid biosynthetic enzyme activity.

The DNA nucleotide sequence of the gene of the present invention is shown in SEQ ID NO: 2 or 4. The gene of the present invention further encompasses a DNA hybridizing to a DNA having a nucleotide sequence complimentary to the nucleotide sequence shown in SEQ ID NO: 2 or 4 under a stringent condition, a DNA having at least 85% or more, preferably 90% or more, more preferably 95% or more, and particularly preferably 97% or more sequence identity with the nucleotide sequence shown in SEQ ID NO: 2 or 4 by calculation using, for example, Basic Local Alignment Search Tool at the National Center for Biological Information (BLAST) based on, for example, default, namely initially set parameters, or a DNA encoding a protein consisting of an amino acid sequence of a protein encoded by the aforementioned DNA with deletion, substitution, insertion, and/or addition of one or several amino acids (1 to 10 amino acids, preferably 1 to 7 amino acids, more preferably 1 to 5 amino acids, even more preferably 1 to 3 amino acids, and still more preferably 1 or 2 amino acids) and having a glycoalkaloid biosynthetic enzyme activity. Here, examples of the "stringent condition" include the condition of about "1×SSC, 0.1% SDS, 37° C.", and examples of a more stringent condition include the condition of about "0.5×SSC, 0.1% SDS, 42° C.", and example of an even more stringent condition include the condition of "0.2×SSC, 0.1% SDS, 65° C." Further, the gene of the present invention encompasses DNA consisting of a degenerate isomer having the nucleotide sequence shown in SEQ ID NO: 2 or 4.

3. Recombinant Vector

The vector of the present invention refers to a recombinant vector into which the aforementioned DNA shown in SEQ ID NO: 2 or 4 is inserted. As the vector, publicly known vectors for yeasts, plant cells, insect cells, and the like can be widely used. Examples of a publicly known vector for yeasts include pDR196, pYES-DEST 52, Yip5, Yrp17, and Yep24, and examples of a publicly known vector for plant cells include pGWB vector, pBiE12-GUS, pIG121-Hm, pBI121, pBiHyg-HSE, pB119, pBI101, pGV3850, and pABH-Hm1, and examples of a publicly known vector for insect cells include pBM030, pBM034, and pBK283. A vector used in the present invention incorporates components involved in the gene expression or suppression such as a promoter, a terminator, and an enhancer. When necessary, the vector used in the preset invention contains a selection marker (for example, a drug-resistant gene, an antibiotic-resistant gene, and a reporter gene). The components involved in the gene expression or suppression are preferably incorporated into a recombinant vector in such a manner that each component can independently function in accordance with the properties of each component. Operations necessary for incorporation of the above components into a vector can be appropriately carried out by those skilled in the art.

4. Transformant

The transformant of the present invention refers to a transformant having the recombinant vector of the present invention. Such a transformant can be obtained by introducing a recombinant vector into which the gene encoding the enzyme is inserted into a host so that the gene of interest is expressed therein. As the host, one that is suitable for the vector can be used. Examples of the host include yeast, a plant cell, an insect cell (such as Sf9), and a plant virus. Preferable examples include yeast, a plant cell, or a plant virus. No particular limitation is imposed on the method for introducing a recombinant vector as long as it is a method for introducing DNA into a microorganism. Examples of such a method include a method using calcium ions [Cohen, S. N. et al.: Proc. Natl. Acad. Sci., USA, 69: 2110 (1972)], an electroporation method, and a tri-parental mating method. Also, examples of a method for producing a plant transformant include a method using a virus, a Ti plasmid or Ri plasmid of *Agrobacterium*, or the like as a vector. Examples of the host plant include a monocotyledonous plant such as rice, barley, and corn and a dicotyledonous plant such as soybean, rapeseed, tomato, and potato. The plant transformant can be obtained by regenerating a plant cell transformed with the gene of the present invention. Regeneration of a plant from a plant cell can be carried out by a routine method.

5. Production of a Glycoalkaloid Biosynthetic Enzyme and a Method for Producing a Glycoalkaloid Compound The glycoalkaloid biosynthetic enzyme of the present invention is a membrane-bound cytochrome P450 monooxidase, and it can be collected from a general plant [Collu et al., 2001, FEBS Lett. 508: 215 to 220, and the like]. Further, the glycoalkaloid biosynthetic enzyme of the present invention can be produced by, for example, mass production employing an expression system using a microorganism such as yeast transformed with the gene of the present invention and an insect cell transformed with the gene of the present invention. Examples of the insect cell include one reported by Morikawa et al. [2006, Plant Cell 18: 1008 to 1022].

Using the aforementioned systems, the glycoalkaloid biosynthetic enzyme of the present invention can be expressed as a highly active protein. Therefore, a glycoalkaloid compound can be produced by adding the substrate for the aforementioned glycoalkaloid biosynthetic enzyme to a culture solution of transformed yeast or insect cells. For example, a large quantity of hydroxylated cholesterols can be efficiently produced by administering, as the substrate, cholesterols to a culture solution of yeast transformants. It has been reported that yeast has the biosynthetic pathway of DMAPP (mevalonate pathway) in cytosol, and that production of a precursor or substrate is enabled by introducing the mevalonate pathway into *Escherichia coli* [Harada and Misawa, 2009 Aug. 12. Epub Appl Microbiol Biotechnol.]. By employing this method, other genes and the membrane-bound cytochrome P450 monooxidase can be expressed at the same time, whereby glycoalkaloids can be produced. For example, Chang et al. reported acquisition of metabolites through expression of a membrane-bound cytochrome P450 monooxidase using *Escherichia coli* [2007 Nat. Chem. Biol. 3: 274 to 277] and Seki et al. reported acquisition of metabolites through expression of a membrane-bound cytochrome P450 monooxidase using yeast [2008 PNAS 105: 14204 to 14209]. Production of a glycoalkaloid compound is enabled by combining the aforementioned methods.

6. Selection of Gene Mutation, Polymorphic Organism, and Gene Expression Mutation The present invention provides a method for detecting the presence of a mutation in the glycoalkaloid biosynthetic enzyme gene, a polymorphism such as a single nucleotide polymorphism (SNP), and a gene expression mutation in a plant. A mutant may be one obtained by radiation, chemical treatment, UV irradiation, or spontaneous mutation.

The above method includes the steps of: isolating genomic DNA and/or RNA from mutant plants and various varieties and breeds of plants, and synthesizing cDNA from the RNA by reverse transcription; amplifying gene fragments containing a glycoalkaloid biosynthetic enzyme gene from the DNA using the DNA amplification technique; and determining the presence of a mutation in the DNA. A commercially available kit (such as DNeasy or RNeasy (QIAGEN)) can be used in a method for extracting DNA or RNA. Also for a method for synthesizing cDNA, a commercially available kit (such as a SuperScript First-Strand System (Invitrogen)) can be used. For a method for amplifying a gene fragment using the DNA amplification technique, the techniques such as so-called PCR and LAMP techniques can be employed. These techniques refer to a group of techniques based on the use of polymerase to achieve amplification (i.e., to increase the number of copies) of a specific DNA sequence by continuous polymerase reactions. This reaction can be employed in lieu of cloning, and what is needed for the above reaction is only the information pertaining to the nucleic acid sequence. In order to carry out DNA amplification, primers complementary to the DNA sequence to be amplified are designed. Subsequently, the designed primers are produced by automatic DNA synthesis. The DNA amplification methods are widely known in the art, and thus those skilled in the art can readily carry out such a method based on the teachings and instructions provided in the present specification. Some methods of PCR (and related techniques) are described in, for example, U.S. Pat. Nos. 4,683,195, 4,683,202, 4,800,159, and 4,965,188, and also in "PCR Protocols: A guide to method and applications" edited by Innis et al.

In the step of determining the presence of a mutation or polymorphism in DNA, a detection method relying on homology between a mutant gene and a normal gene may be used. Examples of such a method include the nucleotide sequencing (Applied Biosystems) and the TILLING method, by which a mutant is detected using an enzyme that cleaves one member of a mismatched pair (Till et al., 2003, Genome Res 13: 524 to 530). The above method can be carried out by comparing the sequence data obtained by the above technique with the nucleotide sequence of a gene segment shown in SEQ ID NO: 2, 4, or 5.

In the step of determining a difference in the amount of mRNA, quantitative PCR such as real-time PCR (for example, a LightCycler, Roche Diagnostics K.K.) may be adopted using the primers produced based on the nucleotide sequence shown in SEQ ID NO: 2 or 4. Then, a difference in the amount of mRNA can be determined by comparing the obtained result with the amount of cDNA obtained from the variety "Sassy."

In a particularly preferable embodiment, the method for determining the presence of a mutation in the glycoalkaloid biosynthetic enzyme gene defined as above is applied to a material obtained from potatoes (*Solanum tuberosum*), which are the plant belonging to the family Solanaceae.

A mutation or polymorphism in the gene encoding a glycoalkaloid biosynthetic enzyme can be identified at the nucleotide level, and further, a plant having a gene encoding a glycoalkaloid biosynthetic enzyme having a mutation and/or polymorphism can be selected by the aforementioned method for detecting a mutation and/or polymorphism. The present invention encompasses the plant having a gene encoding a glycoalkaloid biosynthetic enzyme having a mutation and/or polymorphism thus obtained.

Also, by determining a mutation or polymorphism, or a difference in the amount of mRNA, and further by analyzing the glycoalkaloid content (the method will be described later), a plant in which the ability to express a gene encoding a glycoalkaloid biosynthetic enzyme or the activity of a glycoalkaloid biosynthetic enzyme is altered can be selected.

Here, alteration in the ability to express a gene encoding a glycoalkaloid biosynthetic enzyme or the activity of a glycoalkaloid biosynthetic enzyme encompasses alteration in the ability to express a gene or activity of a glycoalkaloid biosynthetic enzyme caused by mutation such as artificially induced mutation, and alteration in the ability to express a gene or activity of a glycoalkaloid biosynthetic enzyme caused by polymorphism.

Modification in the activity of a glycoalkaloid biosynthetic enzyme in a plant caused by mutation refers to a modification with respect to an existing variety included in the species of the plant. Such existing varieties include wild-type. However, even if a wild-type variety is a naturally emerging variety, it is not included in the existing varieties unless it has a history of industrial application. The existing variety refers to all of the varieties that exist when a plant in which the activity of a glycoalkaloid biosynthetic enzyme is modified is obtained, and encompasses a variety produced by artificial manipulation such as hybridization and gene manipulation. Also, pertaining to modification of activity, it need not be modified with respect to all the existing varieties. As long as the activity is modified with respect to a specific existing variety, then a plant having such a modification is encompassed by the "plants in which the activity of a glycoalkaloid biosynthetic enzyme is modified." The "plants in which the activity of a glycoalkaloid biosynthetic enzyme is modified" also encompass plants in which the activity is modified by spontaneous mutation in the absence of artificial manipulation. By the method of the present invention, a plant in which the activity is spontaneously altered can be selected, and such a plant can be established as a new variety. In addition, when a plant in which the activity of a glycoalkaloid biosynthetic enzyme is modified is produced by applying mutagenesis treatment to an existing variety, a plant serving as a comparison subject with which the plant thus produced is compared may be the same existing variety as that subjected to mutagenesis treatment or an existing variety different from the variety subjected to mutagenesis treatment. Further, it is also possible to fix a mutation in the gene encoding a glycoalkaloid biosynthetic enzyme by crossing plants having a mutation or polymorphism in the gene encoding a glycoalkaloid biosynthetic enzyme, which are selected from nature or produced by mutagenesis treatment, to obtain a plant in which the ability to express the gene encoding a glycoalkaloid biosynthetic enzyme or activity of a glycoalkaloid biosynthetic enzyme is modified as a new plant variety.

When the plant is potato (*Solanum tuberosum*), examples of existing varieties include "Cynthia", "Sassy", "Cheme", "Irish Cobbler (i.e., Danshaku)", "May Queen", and "Sayaka (Ministry of Agriculture, Forestry and Fisheries registration number: Norin No. 36)." Here, a plant in which the ability to express a gene encoding a glycoalkaloid biosynthetic enzyme or activity of a glycoalkaloid biosynthetic enzyme is modified with respect to an existing variety encompasses a plant in which the ability to express a gene encoding a glycoalkaloid biosynthetic enzyme is enhanced or reduced with respect to an existing variety. Further, the above plant encompasses a plant in which the activity of a glycoalkaloid biosynthetic enzyme is increased or decreased with respect to an existing variety. The present invention also encompasses a plant in which the ability to express a gene encoding a glycoalkaloid biosynthetic enzyme or activity of a glycoalkaloid biosynthetic enzyme is modified with respect to an existing variety such as ones described above.

A plant in which the activity of a biosynthetic enzyme of a glycoalkaloid, which is a toxic substance, is decreased is particularly preferable. Such a plant synthesizes a small amount of glycoalkaloid biosynthetic enzymes, or is unable to synthesize the enzyme. Consequently, in such a plant, the content of glycoalkaloid biosynthetic enzyme is low or the enzyme is absent, or the activity of a glycoalkaloid biosynthetic enzyme is low or lost. As a result, in such a plant, the glycoalkaloid content is also low or glycoalkaloid is nonexistent. For example, when the plant is potato, glycoalkaloids such as chaconine and solanine are not synthesized, and thus the amount of glycoalkaloids such as chaconine and solanine synthesized and present in the potato tubers is low. Further, when the plant is tomato, the amount of glycoalkaloids such as tomatine synthesized and present in tomato fruits is low.

In a potato plant in which the activity of a glycoalkaloid biosynthetic enzyme is low or lost, glycoalkaloids such as chaconine and solanine are not synthesized in the tubers, or the amount of glycoalkaloids such as chaconine and solanine synthesized in the tubers is lower than that in the aforementioned existing varieties, and so the amount of glycoalkaloids such as chaconine and solanine present in the tubers is also low.

7. Analysis and Purification of Glycoalkaloids

As the method for analyzing the glycoalkaloid content and the method for purifying a glycoalkaloid, a method employing liquid chromatography such as ones reported by Matsuda et al. (Phytochem. Anal. 15: 121 to 124, 2004) and Kozukue et al. (J. Agric. Food Chem. 52: 2079 to 2083, 2004) are known. However, there are problems that sample pretreatment is complicated, the detection limit is not sufficiently high, and the use of a strong acid imposes great stress on the column and apparatus. Accordingly, in the present invention, the method employing liquid chromatography with an alkali-resistant column for reverse-phase chromatography can be used (an application pertaining to this method was filed as JP Patent Application No. 2009-170317 and published as JP Patent Publication (Kokai) No. 2001-027429 A). GAs (glycoalkaloids) can be efficiently purified and highly precisely analyzed by the above method. An example of application of this method to potatoes is demonstrated in Example 5.

Any column can be used as a column to be used in the above method as long as it has excellent alkali-resistance. As a column having excellent alkali-resistance, for example, an ethylene-crosslinked column can be used. Preferably, a column of XBridge™ brand (Nihon Waters K.K.) is used. The Waters XBridge™ Shield RP18 (Nihon Waters K.K.) and the Waters XBridge™ C18 are particularly preferable. According to the method of the present invention, the XBridge™ Shield RP 18 column and the Waters XBridge™ C18 column each have advantages in that the former requires a short time per sample, while the latter has high durability.

As a mobile phase to be used for liquid chromatography, an alkaline buffer can be used. Preferably, a volatile alkaline buffer is used. When a sample purified by liquid chromatography is subjected to mass spectrometry, a volatile alkaline buffer is conveniently used as a mobile phase since it does not remain in the sample. As the volatile alkaline buffer, for example, triethylamine and ammonium hydrogen carbonate can be used, of which ammonium hydrogen carbonate is preferably used for its high buffering effects.

The concentration of ammonium hydrogen carbonate used as a mobile phase is 5 to 20 mM, preferably 5 to 15 mM, and more preferably 10 mM. The pH of ammonium hydrogen carbonate can be adjusted preferably to 9.0 to 11.0 and more preferably to 10.0. Adjusting the pH of the mobile phase to 10.0 further improves the buffering ability of ammonium hydrogen carbonate.

GAs may be eluted into a mobile phase by the isocratic method or the gradient method using an alkaline buffer and an organic solvent. However, GAs are preferably eluted by the isocratic method, which involves simple operations.

Examples of an organic solvent to be used for a mobile phase include, but are not limited to, methanol, ethanol, tetrahydrofuran (THF), and acetonitrile (MeCN). Preferably, MeCN is used.

In the isocratic method, an alkaline buffer and an organic solvent, preferably aqueous ammonium hydrogen carbonate and MeCN are appropriately used at a ratio of 30 to 70:70 to 30, preferably 40 to 60:60 to 40 according to the GAs of interest. For example, when the GAs of interest are α-solanine or α-chaconine, an alkaline buffer and an organic solvent, preferably aqueous ammonium hydrogen carbonate and MeCN are used at a ratio of 40:60, and when the GAs of interest are α-tomatine, the aforementioned solutions are used at a ratio of 60:40.

Liquid chromatography can be carried out using a commercially available HPLC apparatus. The column can be appropriately equilibrated and the flow rate can be appropriately set according to the column size and sample volume.

Fractions obtained by liquid chromatography can be analyzed by mass spectrometry, a UV or multi-wavelength detector, or the like to be described below.

A plant-derived sample is preferably partially purified by pretreatment as described below prior to liquid chromatography.

A plant-derived sample contains not only GAs, but also various polymeric impurities such as starch, proteins, and cellulose. Thus, polymeric impurities contained in the sample need to be removed and GAs need to be partially purified and washed to achieve efficient purification and highly precise analysis of GAs.

As a method for removing polymeric impurities, a method generally used by those skilled in the art, such as an alcohol precipitation method, can be used. As the alcohol, ethanol or methanol can be used, of which methanol is preferable. In applying this method, acid is added to alcohol so as to efficiently extract GAs in the form of a salt. Examples of the acid that can be used include, but are not limited to, acetic acid, hydrochloric acid, and formic acid. Preferably, formic acid is added. The amount of acid added to alcohol can be appropriately determined within such a range that the GAs of interest are not destroyed. When formic acid is used, it is added to alcohol so as to achieve a concentration of 0.1 to 2% (v/v), preferably 0.1% (v/v). When an acid other than formic acid is used, it can be added so as to achieve a normality equivalent to that achieved by formic acid added as above.

It is to be noted that the conventional sample preparation method (see Matsuda et al., Phytochem. Anal. 15: 121 to 124, 2004) has required lengthy and complex pretreatment, which involved an extended period of homogenization of samples, followed by multiple centrifugations for removal of a large amount of polymeric impurities such as starch contained in the sample and filtering of the resulting product. Meanwhile, according to the preparation method of the present invention, a sample can be readily prepared in a short time since polymeric impurities such as starch can be removed from the pulverized plant pieces by alcohol precipitation in a short time.

After alcohol precipitation, the supernatant containing GAs is diluted with an acid such as 0.1 to 2% (v/v) formic acid or acetic acid, preferably 0.1% (v/v) formic acid, and then subjected to liquid chromatography under the aforementioned conditions.

Fractions purified by liquid chromatography can be further subjected to mass spectrometry. In this case, mass spectrometry may be carried out by LC-MS, which is a technique that combines liquid chromatography with mass spectrometry.

Mass spectrometry can be carried out by single-focusing magnetic sector mass spectrometry, double-focusing magnetic sector mass spectrometry, quadrupole mass spectrometry, quadrupole ion trap mass spectrometry, time-of-flight mass spectrometry, ion-cyclotron mass spectrometry (Fourier transform mass spectrometry), and the like.

As a method to ionize a sample for mass spectrometry, the electron ionization (EI) method, the chemical ionization (CI) method, the desorption electron ionization (DEI) method, the desorption chemical ionization (DCI) method, the fast atom bombardment (FAB) method, the FRIT-fast atom bombardment (FRIT-FAB) method, the electrospray ionization (ESI) method, the matrix-assisted laser desorption ionization (MALDI) method, and the like can be employed.

Various conditions used for mass spectrometry are specifically described in the Examples; however, the conditions are appropriately set by those skilled in the art according to the type of GAs used as an analyte.

An analytical standard sample of GAs is analyzed by LC-MS and a calibration curve can be produced in accordance with a method generally used by those skilled in the art. While β-D-glucosamine pentaacetate can be used as an internal standard substance for a potato-derived sample, particularly in the α-solanine and α-chaconine analysis system, brassinolide is preferably used, which has the steroid skeleton, similarly to α-solanine and α-chaconine. Meanwhile, a water-soluble amine is preferably used for a tomato-derived sample, particularly in the α-tomatine analysis system. Examples of the water-soluble amine that can be used as an internal standard substance include serine methyl ester and alanine methyl ester, of which alanine methyl ester is particularly preferable for its strong retention on the column. Accordingly, the reliability of quantitative analysis can be remarkably improved by using brassinolide for a potato-derived sample and alanine methyl ester for a tomato-derived sample.

According to the method of the present invention, a column having a size that is widely used for HPLC can be used, and thus the conditions used herein can be directly applied also to analysis using a UV or multi-wavelength detector.

EXAMPLES

Hereinbelow, the present invention will be described in greater detail with reference to the Examples. However, the present invention is not limited to these Examples.

Example 1

Acquisition of the Full-Length Sequence of the Candidate Glycoalkaloid Biosynthetic Gene E Extraction of mRNA from the sprouts of a variety of potato (*Solanum tuberosum*), "Sassy", was carried out using RNeasy (QIAGEN). Total cDNA synthesis was carried out using a SuperScript First-Strand System (Invitrogen). While the aglycone of a glycoalkaloid is presumed to be formed from cholesterol, this has not been verified (Non-Patent Literature 1). However, even assuming that the aglycone is formed from a cholesterol-related compound, there must be some hydroxylation steps. In the steps of hydroxylation, the possible involvement of at least three types of enzymes, namely cytochrome P450 monooxygenase, dioxygenase, and NADPH-flavin reductase, is considered. Of these, cytochrome P450 monooxygenase was designated as a target, and as a gene expressed in potatoes, the TC155233 gene, for which many EST clones have been isolated from the sprouts, was focused based on the information published in the DFCI Potato Gene Index (compbio.dfci.harvard.edu/tgi/plant.html) Release 11.0.

Based on the sequence of the above gene, PCR was performed (PCR conditions: 95° C. for 5 minutes, 30 cycles of (95° C. for 30 seconds, 55° C. for 30 seconds, and 72° C. for 3 minutes), and 72° C. for 10 minutes) using the primers [U890: GAGGCTAAGAAAAAGAGAGAGAGA (SEQ ID NO: 6) and U889: CGTTCTACAAAAACATCCAATTT (SEQ ID NO: 7)]. The amplification product was subjected to cloning using a TOPOTA cloning kit for sequencing (Invitrogen). Further, the PCR product was sequenced by ABI310 (Applied Biosystems). The sequence containing ORF is shown in SEQ ID NO: 2 and the amino acid sequence of an enzyme encoded by the sequence of the cDNA is shown in SEQ ID NO: 1.

It should be noted that the homologous gene of tomato corresponds to SGN-U583521 in the Sol Genomics Network (solgenomics.net/index.pl). The sequence containing ORF is shown in SEQ ID NO: 4 and the amino acid sequence of an enzyme encoded by the sequence of the cDNA is shown in SEQ ID NO: 3. As a result of comparison of the nucleotide sequences of these genes, 95% homology was observed. Similarly in the Sol Genomics Network, the genomic structure of the genome sequence of this homologous gene of tomato is disclosed as SL1.00sc03540, which is reported to contain seven introns. However, the above website has not mentioned the function of the gene at all (FIG. 1).

Example 2

Isolation of the Genomic Gene of the Candidate Glycoalkaloid Biosynthetic Gene E Genomic DNA was extracted from "Sassy" using RNeasy (QIAGEN). PCR was performed using the same primers as those used in Example 1 and (U904: TGATAAGGAAATC-CTGGGAGA (SEQ ID NO: 8) and U901: AGAGAAGC-CATGAAGGATGG (SEQ ID NO: 9)), and further, for the second intron, using PrimeSTAR HS DNA Polymerase (TAKARA BIO INC.) as the enzyme and (U898: GAAATACGCTACTACGGAAGAACC (SEQ ID NO: 10) and U899: CGTCATTTGCCTAATCTCATC (SEQ ID NO: 11)) as the primers, whereby the full-length genomic DNA was sequenced (SEQ ID NO: 5). It was revealed that there were seven introns. (Example 3) Vector construction for the production of a transformant in which the candidate glycoalkaloid biosynthetic gene E is suppressed As to the method for suppressing the above gene by transformation, a reverse complementary gene fragment configured to be driven by a strong promoter was expressed (which is generally referred to as the RNAi method for plants) (Chuang and Meyerowitz, Proc Natl Acad Sci, USA, 97, 4985 to 90 (2000); Wesley et al., Plant J., 27, 581 to 90 (2001)). The full-length cDNA obtained in Example 1 was subjected to PCR (PCR conditions: 95° C. for 5 minutes, 30 cycles of (95° C. for 30 seconds, 55° C. for 30 seconds, and 72° C. for 30 seconds), and 72° C. for 10 minutes) using the primers [U675: GAGCTCTAGAGGTTTGGGACAGGAG-GAAT (SEQ ID NO: 12) and U676: GGATCCATATG-CAAGCCTGTGCATCTTAT (SEQ ID NO: 13)], whereby a gene fragment was obtained. Based on the binary vector pKT11 (JP Patent Publication (Kokai) No. 2001-161373 A), a vector pKT230 for transformation of plants was prepared by ligating a cauliflower mosaic virus 35S RNA promoter, the above gene fragment (in the forward direction), the third intron of the *Arabidopsis thaliana* phytoene desaturase gene (AT4g14210), the above gene fragment (in the reverse direction), and a nopaline synthase terminator in the above order (FIG. 2).

Example 4

Production of a Transformed Potato Plant

The vector prepared in Example 3 was introduced into the *Agrobacterium tumefaciens* GV3110 strain by the electroporation method (Gelvin and Schilperoor, Plant Molecular Biology Manual, C2, 1 to 32 (1994), Kluwer Academic Publishers). The *Agrobacterium tumefaciens* GV3110 strain containing the vector was subjected to shaking culture at 28° C. for 12 hours in a YEB liquid medium (5 g/l beef extract, 1 g/l yeast extract, 5 g/l peptone, 5 g/l sucrose, and 2 mM magnesium sulfate (pH 7.2)) containing 50 ppm kanamycin. The resulting culture solution (1.5 ml) was centrifuged at 10,000 rpm for three minutes to collect the bacteria, which were washed with 1 ml of an LB medium for removal of kanamycin. Further, centrifugation was performed at 10,000 rpm for three minutes to collect the bacteria, which were resuspended in 1.5 ml of an MS medium containing 3% sucrose (Murashige and Skoog, Physiol. Plant., 15, 473 to 497 (1962)), and the resulting solution was provided as a bacterial solution for infection.

Transformation of potato was carried out according to [Monma (1990), Plant Biotechnology 7: 57 to 63]. Microtubers obtained from the potato variety "Sassy" (Kirin Agribio Co., Ltd.) were sliced to a thickness of 2 to 3 mm, which were provided as the materials for the infection of *Agrobacterium*. The resulting slices were immersed in the aforementioned Agrobacterial solution and placed on sterilized filter paper so as to remove excess *Agrobacteria*. The slices were then placed on an MS medium (supplemented with 1 ppm zeatin, 0.1 ppm IAA, 100 μM acetosyringone, and 0.8% agar) in a petri dish. The slices were then cultured under the conditions of 25° C., illumination for 16 hours (at a photon flux density of 32 μE/m² s)/non-illumination for 8 hours for three days. Subsequently, the slices were cultured in a medium containing 250 ppm carbenicillin in place of acetosyringone for one week. Thereafter, the slices were transferred onto a medium containing 50 ppm kanamycin, followed by subculture at 2-week intervals. During subculture, adventitious buds were formed and shoots grew. The elongated shoots were placed on an MS medium containing 250 ppm carbenicillin and 100 ppm kanamycin without plant growth regulators. A plant having a kanamycin-resistant gene as an exogenous gene was detected among kanamycin-resistant, grown plants by subjecting the rooting shoots to PCR (PCR conditions: 95° C. for 5 minutes, 30 cycles of (95° C. for 30 seconds, 55° C. for 30 seconds, and 72° C. for 1 minute), and 72° C. for 10 minutes), whereby the regenerated plant was confirmed to be a plant transformant. Here, the following primers were used as the primers for specifically amplifying the kanamycin-resistant gene sequence: TAAAGCACGAGGAAGCGGT (SEQ ID NO: 14) and GCACAACAGACAATCGGCT (SEQ ID NO: 15). From the above, 30 lines of transformed potato plants into which the vector pKT230 was introduced were obtained.

Example 5

Analysis of the Glycoalkaloid Content and the Expression of the Candidate Gene E in the Plant Transformant The In vitro stems of the 30 lines obtained in Example 4 grew for one month after subculture. Then, two to four stems were collected to adjust the weight to approximately 100 mg, in which the glycoalkaloid content was measured by the following method employing liquid chromatography with a column for alkali-resistant reversed-phase chromatography (an application pertaining to this method was filed as JP Patent Application No. 2009-170317). Analysis of GAs (α-solanine and α-chaconine) contained in potatoes 1. Sample Preparation The In vitro stems of the 30 plants obtained in Example 4 were elongated for one month after subculture. Then, two to four stems were collected to adjust the weight to approximately 100 mg, to which 990 μL of 0.1% formic acid in 80% MeOH aq. and, as an internal standard, 10 μg/10 μL brassinolide (Brassino Co., Ltd.) were added, followed by homogenization using a mixer mill (¹/₂₅ sec, 5 min, 4° C.). The homogenized samples thus obtained were centrifuged (10,000 rpm, 5 min), followed by alcohol precipitation. Then, 25 μL of the supernatant was collected and made up to 500 μL with 0.1% aqueous formic acid. The resulting sample was subjected to LC-MS under the following conditions using LCMS-2010EV (Shimadzu Corporation) as an LC-MS apparatus.

2. LC-MS Conditions (i) LC Conditions

An ethylene-crosslinked column (XBridge™ Shield RP 18-5 (diameter of 2.1×150 mm, Nihon Waters K. K.)) having excellent alkali resistance was employed for the LC system. For the mobile phase, a mobile phase A: 10 mM aqueous ammonium hydrogen carbonate (pH 10) and a mobile phase B: MeCN were used at a ratio of A:B=40:60 with respect to the aforementioned sample solvent under the isocratic conditions. Other conditions used were as follows:
Flow rate: 0.2 mL/min
Column oven: 40° C.

(ii) MS Conditions

First of all, the MS spectrum of each component was confirmed by scan mode (see FIG. 3). From the results, a detection method including: SIM mode m/z: 481 (brassinolide), 869 (α-solanine), and 853 (α-chaconine) was used.

Other MS conditions used were as follows.
MS detection: Positive ion mode
Ionization method: ESI
Event time: 1 sec
Detector voltage: 1.5 kV
Analysis time: 8 min 3. Creation of Calibration Curves Using the Standard Products of α-Solanine, α-Chaconine, and Brassinolide Two mg of α-solanine (Wako Pure Chemical Industries, Ltd.) and 2 mg of α-chaconine (Sigma-Aldrich Co. LLC.) were each separately dissolved in 1 mL of 0.1% (v/v) aqueous formic acid (each resulting in a 2 μg/μL solution). Equal volumes of these two different solutions were mixed to prepare a 1 μg/μL (=1000 ng/μL) solution of α-solanine and α-chaconine. The resulting solution was serially diluted 10-fold with 0.1% (v/v) aqueous formic acid and subjected to LC-MS to create a calibration curve. Also, the detection limits of both of the above substances were obtained.

One mg of brassinolide (Brassino Co., Ltd.) was dissolved in 1 mL of a MeOH solution (1 μg/μg). The resulting solution was serially diluted 10-fold with 50% (v/v) aqueous MeOH and then subjected to LC-MS to create a calibration curve.

The calibration curves created for each of α-solanine, α-chaconine, and brassinolide are shown in FIG. 4. As shown in FIG. 4, good linearity was achieved for α-solanine and α-chaconine in a range of 0.05 to 50 ng with a confidence coefficient of 0.99 or greater. For both substances, when the content exceeded 100 ng, signal saturation occurred, resulting in loss of linearity. Further, the detection limit was 0.02 ng (2 μl per injection) for both of the substances.

Meanwhile, good linearity was achieved for brassinolide in a range of 2 to 200 ng (see FIG. 4). When the content was 500 ng or more, signal saturation also occurred similarly to the above.

Figure 5:
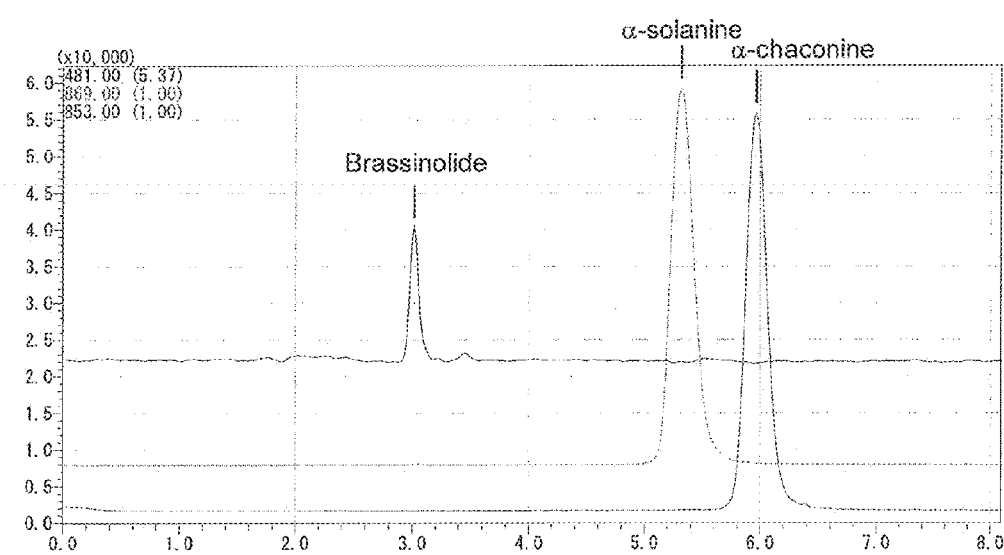
FIG. 5 shows LC-MS chromatograms of the standard products (α-solanine, α-chaconine, and brassinolide).

Typical chromatograms obtained using the standard products of α-solanine, α-chaconine, and brassinolide were shown in FIG. 5.

4. LC-MS Analysis of GAs in Potatoes Using Brassinolide as the Internal Standard Each sample prepared in the aforementioned 1. (10 μl or 20 μL) was injected into an LC-MS system under the aforementioned conditions.

The recovery rate of the internal standard brassinolide was found to be 50 to 110%. Correction was carried out based on the quantitative value of brassinolide, and the contents of α-solanine and α-chaconine in each sample were quantitated based on the above calibration curves. The contents of α-solanine and α-chaconine per 100 mg sample (FW) were then calculated.

Figure 6:
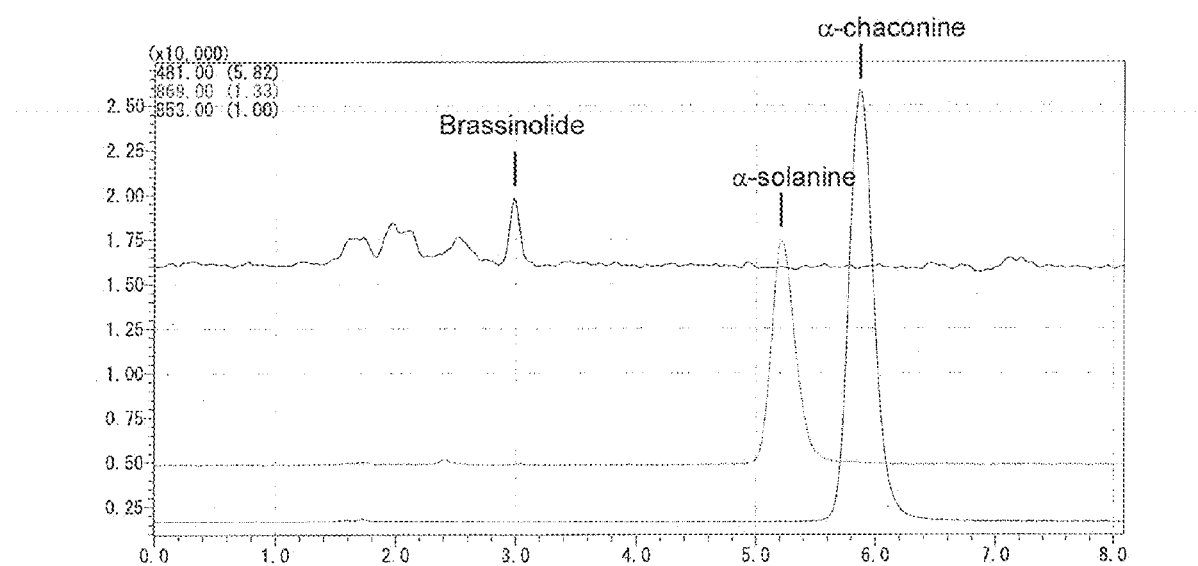
FIG. 6 shows LC-MS chromatograms of α-solanine, α-chaconine, and brassinolide in a stem-derived sample.

Typical chromatograms obtained by this analysis are shown in FIG. 6.

Figure 7:
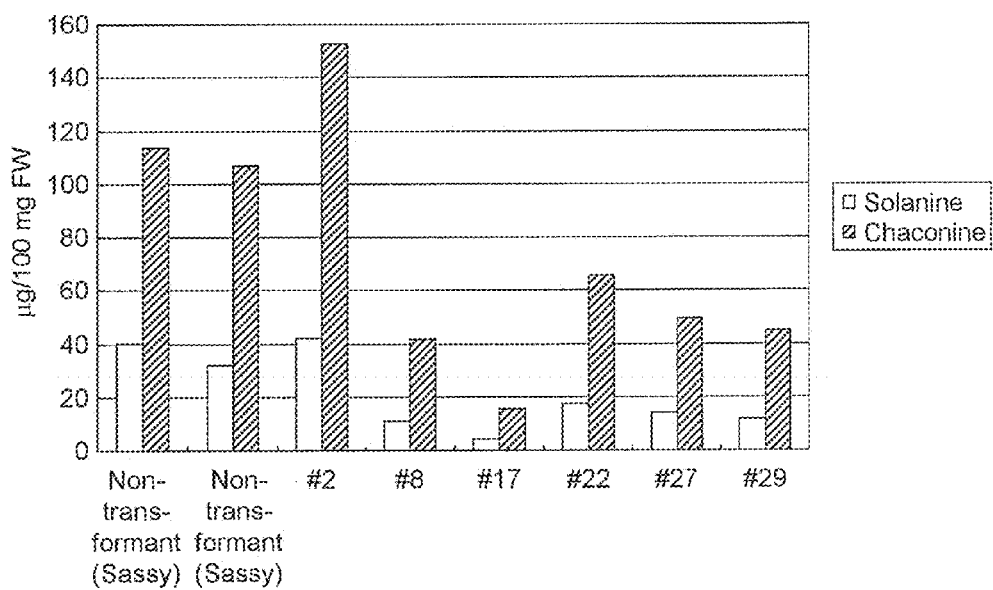
FIG. 7 shows the glycoalkaloid contents in the in vitro stems of potato transformants. Each error bar indicates the standard deviation.
Figure 8:
FIG. 8 shows the results of RT-PCR of mRNA extracted from the in vitro stems of potato transformants.

The amounts of glycoalkaloids accumulated in five lines (#8, #17, #22, #27, and #29) out of the 30 plants were found to be low with good reproducibility. Based on this finding, the in vitro stems of the five lines, one line (#2), in which the amount of glycoalkaloids accumulated was not low, and two control plants into which the gene was not introduced were homogenized by liquid nitrogen. A half portion of each homogenized sample was used for measuring the glycoalkaloid content. From the other half portion, mRNA was extracted using RNeasy (QIAGEN), and total cDNA was synthesized using a SuperScript First-Strand System (Invitrogen). In the above plants, the amounts of glycoalkaloids accumulated were extremely lower than those in non-transformants (two plants) (FIG. 7). Further, as a result of RT-PCR (PCR conditions: 95° C. for 5 minutes, 25 cycles of (95° C. for 30 seconds, 55° C. for 30 seconds, and 72° C. for 3 minutes), and 72° C. for 5 minutes) using the primers [U887: TAAGGGACTCAAGGCTCGAA (SEQ ID NO: 16) and U886: TTCCTCTTTGGCTTTCTCCA (SEQ ID NO: 17)], it was found that mRNA expression was either extremely low or unobservable in any of the above plants (FIG. 8). These results indicated that suppression of the gene expression of the candidate gene E led to an extremely reduced accumulation of glycoalkaloids, revealing that the candidate gene E was a gene encoding a glycoalkaloid biosynthetic enzyme. These five lines of in vitro plants and the non-transformant were allowed to proliferate, and three plants from each line were habituated to commercially available culture soil for vegetables, and then cultivated in a biohazard greenhouse according to a general method to harvest tubers. Each plant from the five lines (#8, #17, #22, #27, and #29) grew in an equivalent manner to the non-transformant and successfully produced equivalent tubers to those produced by the non-transformant (Table 1).

TABLE 1

| Line No. | Number of tubers | Standard deviation | Average weight (g) per tuber | Total weight (g) per plant | Standard deviation |
|---|---|---|---|---|---|
| Non-transformant | 15.0 | 3.6 | 17.7 | 260.2 | 35.3 |
| #8 | 21.0 | 6.2 | 14.3 | 291.3 | 39.9 |
| #17 | 19.7 | 3.8 | 15.6 | 297.9 | 17.8 |
| #22 | 18.3 | 3.8 | 18.3 | 321.3 | 37.2 |
| #27 | 24.3 | 4.0 | 15.1 | 360.3 | 16.2 |
| #29 | 19.7 | 4.5 | 19.7 | 268.2 | 50.8 |

Figure 9:
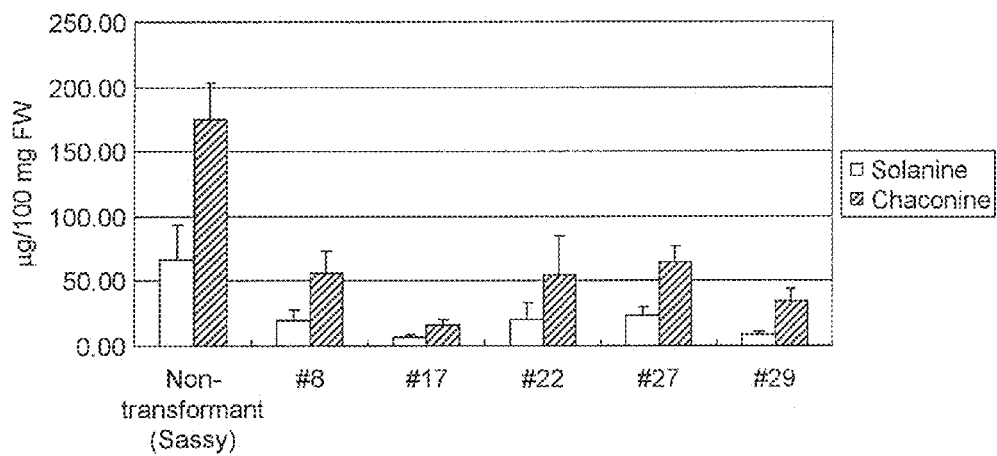
FIG. 9 shows the glycoalkaloid contents in the tuber epidermis of potato transformants. Each error bar indicates the standard deviation.

Further, the epidermis of the center part of each of the three harvested tubers was peeled at a thickness of about 1 mm, in which the glycoalkaloid content was similarly analyzed. As a result, surprisingly, the glycoalkaloid content in the tubers was found to be extremely low, and it was confirmed that even in comparison with the glycoalkaloid content in "Sayaka" measured by the same method, where "Sayaka" is a variety known for its low glycoalkaloid content, the glycoalkaloid content in the above harvested tubers was lower (FIG. 9).

Example 6

Production of a Transformed Tomato Plant

Figure 10:
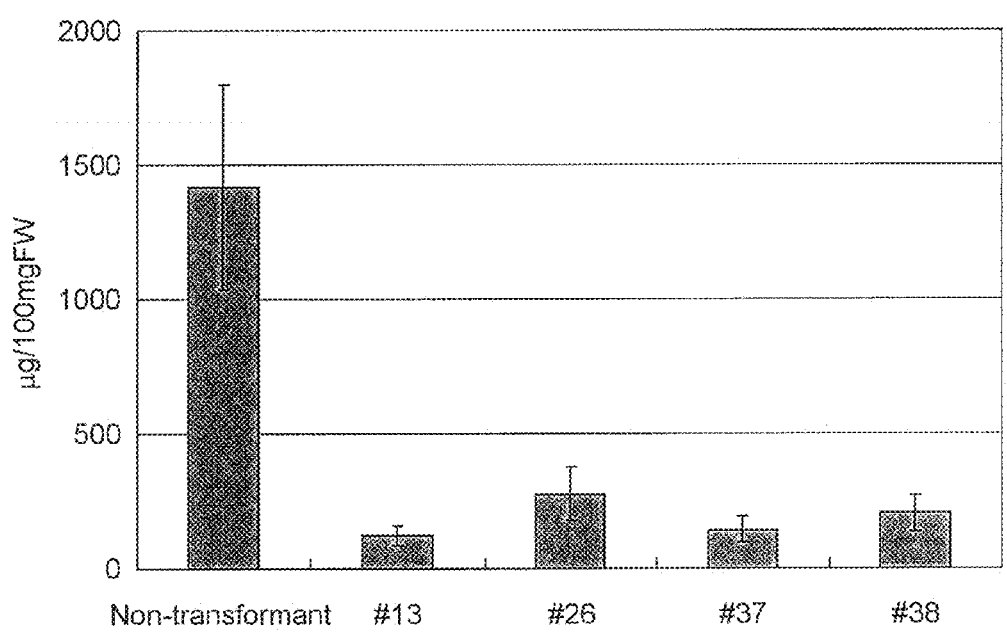
FIG. 10 shows the glycoalkaloid contents in young leaves of tomato transformants. Each error bar indicates the standard deviation.

Transformation of tomatoes was performed according to [Sun et al. (2006) Plant Cell Physiol. 47: 426 to 431]. The *Agrobacterium tumefaciens* AGLO strain containing the vector pKT230 prepared in (Example 3) was cultured to give a bacterial solution for infection. Sections of 5 mm or smaller taken from the cotyledons of the experimental line of tomatoes (*Solanum lycopersicum*) called "Micro-Tom" obtained by sterile seeding were immersed in the aforementioned *Agrobacterium* suspension for 10 minutes to allow infection to take place. The sections were then placed on sterilized filter paper for removal of excess *Agrobacteria*. The leaves were placed on a coculture MS medium (containing 1.5 mg/l zeatin, 40 μM acetosyringone, and 0.3% Gelrite®) [Murashige and Skoog, Physiol. Plant., 15, 473 to 497 (1962)] in a petri dish. The petri dish was placed in a dark place and culture was performed at 25° C. for three days. The sections were subjected to subculture at 2-week intervals in a selective MS medium 1 (containing 1.5 mg/l zeatin, 100 mg/l kanamycin, 375 mg/l augmentin, and 0.3% Gelrite®) under the conditions of illumination for 16 hours (at a photon flux density: 32 μE/m$^2$ s)/non-illumination for 8 hours at 25° C. During subculture, adventitious buds were formed and shoots grew. In order to further elongate the shoots, the shoots were transplanted to a selective MS medium 2 (containing 1.0 mg/l zeatin, 100 mg/l kanamycin, 375 mg/l augmentin, and 0.3% Gelrite®). The elongated shoots were rooted in a selective ½ concentration MS medium (containing 100 mg/l kanamycin, 375 mg/l augmentin, and 0.3% Gelrite®). A plant having a kanamycin-resistant gene as an exogenous gene was detected among kanamycin-resistant, grown plants by subjecting the rooting shoots to PCR (PCR conditions: 95° C. for 5 minutes, 30 cycles of (95° C. for 30 seconds, 55° C. for 30 seconds, and 72° C. for 1 minute), and 72° C. for 10 minutes), whereby the regenerated plant was confirmed to be a plant transformant. Here, the following primers were used as the primers for specifically amplifying the kanamycin-resistant gene sequence: TAAAGCACGAGGAAGCGGT (SEQ ID NO: 18) and GCACAACAGACAATCGGCT (SEQ ID NO: 19). From the above, 13 lines of transformed tomato plants into which the vector pKT230 was introduced were obtained. These 13 plants were habituated in a greenhouse and cultivated for about one month. From each of three newly developed young leaves, about 100 mg was weighed out, and in a similar manner to potatoes, the glycoalkaloid content in the pieces of leaves was measured by the method employing liquid chromatography with a column for alkali-resistant reverse-phase chromatography as used in Example 5. It is to be noted that with regard to the analytical conditions, for the mobile phase, a mobile phase A: 10 mM aqueous ammonium hydrogen carbonate (pH 10) and a mobile phase B: MeCN were used at a ratio of A:B=40:60 with respect to the aforementioned sample solvent under the isocratic conditions. It was found that four out of 13 lines had a remarkably low tomatine content of 280 μg or less per 100 mg fresh weight, which was ⅕ of the control (FIG. 10).

Example 7

Screening for a Plant Having a Mutant Candidate Glycoalkaloid Biosynthetic Gene E From 10 in vitro plants (provided by Okamura, the senior research scientist in Kirin Agribio Co., Ltd.), which were obtained by subjecting the potato variety "Sassy" to mutation treatment involving particle beam irradiation (NIRS-HIMAC irradiation apparatus; 0.1 to 3 Gy argon ion beams (500 MeV/nucleon), 0.2 to 3 Gy neon ion beams (400 Mev/nucleon), or 0.5 Gy to 5Gy carbon ion beams (290 MeV/nucleon)), leaves were obtained. From those leaves, genomic DNA was extracted using DNeasy. The structural gene of the genomic DNA was subjected to PCR using the primers [U890: GAGGCTAAGAAAAAGAGAGAGAGA (SEQ ID NO: 6), U889: CGTTCTACAAAAACATC-CAATTT (SEQ ID NO: 7), U904: TGATAAGGAAATC-CTGGGAGA (SEQ ID NO: 8), and U901: AGAGAAGC-CATGAAGGATGG (SEQ ID NO: 9)), and further, for the second intron, using PrimeSTAR HS DNA Polymerase (TAKARA BIO INC.) as the enzyme and (U898: GAAATACGCTACTACGGAAGAACC (SEQ ID NO: 10) and U899: CGTCATTTGCCTAATCTCATC (SEQ ID NO: 11)] as the primers, whereby the gene region was obtained. Further, cloning was carried out using a TOPOTA cloning kit for sequencing. Further, the PCR product was sequenced by ABI310. As a result, no line was found to carry a mutant gene out of the 10 plants provided this time. However, it is possible to acquire a plant having a mutant gene by repeatedly applying the above operations to a plant that has been subjected to thorough mutation treatment.

INDUSTRIAL APPLICABILITY

The glycoalkaloid biosynthetic enzyme of the present invention and the method for producing and examining an organism using the gene of the above enzyme are useful for the development of production of a glycoalkaloid compound using an organism such as a plant and selection of a variety of plant belonging to the family Solanaceae such as potatoes.
Free Text Of Sequence Listings
Primers: SEQ ID NOs: 6 to 19
All the publications, patents, and patent applications cited in the present specification are incorporated herein by reference in their entirety.

The invention claimed is:

1. A recombinant vector comprising a gene consisting of the DNA of any one of the following (a) to (f):
   (a) a DNA consisting of the nucleotide sequence shown in SEQ ID NO: 2;
   (b) a DNA consisting of a nucleotide sequence having 80% or more sequence identity with the nucleotide sequence shown in SEQ ID NO: 2;
   (c) a DNA consisting of a degenerate isomer of the nucleotide sequence shown in SEQ ID NO: 2,
   (d) a DNA consisting of the nucleotide sequence shown in SEQ ID NO: 4;
   (e) a DNA consisting of a nucleotide sequence having 80% or more homology with the nucleotide sequence shown in SEQ ID NO: 4; and
   (f) a DNA consisting of a degenerate isomer of the nucleotide sequence shown in SEQ ID NO: 4;
   wherein said gene encodes a glycoalkaloid biosynthetic enzyme in a plant belonging to the family Solanaceae.

2. A transformant into which the recombinant vector according to claim 1 is introduced.

3. The transformant according to claim 2, which is a plant.

4. A method for selecting a plant belonging to the family Solanaceae comprising at least one mutation and/or polymorphism, comprising:
   (i) isolating a nucleic acid from a candidate plant belonging to the family Solanaceae, the nucleic acid being a genomic DNA or an RNA;
   (ii) when the nucleic acid in (i) is the RNA, synthesizing a cDNA by reverse transcription;
   (iii) amplifying a gene fragment comprising a nucleotide sequence corresponding to the nucleotide sequence shown in SEQ ID NO: 2, 4, or 5 from the DNA obtained by the step (i) or (ii);
   (iv) determining a presence of a mutation and/or polymorphism in the DNA by determining the sequence homology of the DNA from the amplified gene fragment from the candidate plant to the corresponding sequence selected from the group consisting of SEQ ID NOs: 2, 4, and 5; and
   (v) selecting and cultivating the plant comprising a mutation and/or polymorphism in the nucleotide sequence corresponding to the nucleotide sequence shown in SEQ ID NO: 2, 4, or 5.

5. The method for selecting a plant according to claim 4, further comprising selecting the plant in which an ability to express the gene comprising the amplified gene fragment or an activity of a glycoalkaloid biosynthetic enzyme encoded by the gene comprising the amplified gene fragment is altered from that in an existing variety.

6. A plant belonging to the family Solanaceae in which an ability to express a gene encoding a glycoalkaloid biosynthetic enzyme or an activity of a glycoalkaloid biosynthetic enzyme encoded by the gene is altered from that in an existing variety, wherein the gene encoding a glycoalkaloid biosynthetic enzyme comprises the nucleotide sequence shown in SEQ ID NO: 2, 4, or 5 and the plant is produced by artificial manipulation.

7. The plant belonging to the family Solanaceae according to claim 6, which is *Solanum tuberosum*.

* * * * *